US012580081B2

(12) United States Patent
Hegde et al.

(10) Patent No.: US 12,580,081 B2
(45) Date of Patent: Mar. 17, 2026

(54) SYSTEMS AND METHODS FOR DIRECTLY PREDICTING CANCER PATIENT SURVIVAL BASED ON HISTOPATHOLOGY IMAGES

(71) Applicant: Verily Life Sciences LLC, South San Francisco, CA (US)

(72) Inventors: Narayan Hegde, Mountain View, CA (US); Yun Liu, Mountain View, CA (US); Craig Mermel, Mountain View, CA (US); David F. Steiner, Mountain View, CA (US); Ellery Wulczyn, Mountain View, CA (US); Po-Hsuan Cameron Chen, Mountain View, CA (US); Martin Stumpe, Mountain View, CA (US); Zhaoyang Xu, Mountain View, CA (US); Apaar Sadhwani, Mountain View, CA (US)

(73) Assignee: Verily Life Sciences LLC, Dallas, TX (US)

( * ) Notice: Subject to any disclaimer, the term of this patent is extended or adjusted under 35 U.S.C. 154(b) by 407 days.

(21) Appl. No.: 18/000,359

(22) PCT Filed: Jul. 7, 2021

(86) PCT No.: PCT/US2021/040726
§ 371 (c)(1),
(2) Date: Nov. 30, 2022

(87) PCT Pub. No.: WO2021/258081
PCT Pub. Date: Dec. 23, 2021

(65) Prior Publication Data
US 2023/0207134 A1     Jun. 29, 2023

Related U.S. Application Data

(60) Provisional application No. 63/039,670, filed on Jun. 16, 2020.

(51) Int. Cl.
| | |
|---|---|
| *G16H 50/30* | (2018.01) |
| *G06N 3/08* | (2023.01) |
| *G06T 7/00* | (2017.01) |

(52) U.S. Cl.
CPC ............... *G16H 50/30* (2018.01); *G06N 3/08* (2013.01); *G06T 7/0012* (2013.01);
(Continued)

(58) Field of Classification Search
None
See application file for complete search history.

(56) References Cited

U.S. PATENT DOCUMENTS

| | | | |
|---|---|---|---|
| 10,650,929 B1 * | 5/2020 | Beck | G06T 7/194 |
| 11,017,532 B1 * | 5/2021 | Beck | G06F 16/55 |

(Continued)

FOREIGN PATENT DOCUMENTS

WO      2019245597 A1    12/2019

OTHER PUBLICATIONS

Jia, Y., Shelhamer, E., Donahue, J., Karayev, S., Long, J., Girshick, R., Guadarrama, S., & Darrell, T. (2014). Caffe: Convolutional Architecture for Fast Feature Embedding. Proceedings of the 22nd ACM International Conference on Multimedia, 675-678. https://doi.org/10.1145/2647868.2654889. (Year: 2014).*

(Continued)

*Primary Examiner* — Amandeep Saini
*Assistant Examiner* — Caroline Tabancay Duffy
(74) *Attorney, Agent, or Firm* — Kilpatrick Townsend & Stockton LLP

(57)     ABSTRACT
One example method includes obtaining one or more histopathology images of a sample from a cancer patient; selecting a plurality of tissue image patches from the one or more histopathology images; determining, by a deep learning system comprising a plurality of trained machine learn-
(Continued)

ing ("ML") models, a plurality of image features for the plurality of tissue image patch, wherein each tissue image patch is analyzed by one of the trained ML models; determining, by the deep learning system, probabilities of patient survival based on the determined plurality of image features; and generating, by the deep learning system, a prediction of patient survival based on the determined probabilities.

25 Claims, 19 Drawing Sheets

(52) U.S. Cl.
     CPC .............. *G06T 2207/10056* (2013.01); *G06T 2207/20081* (2013.01); *G06T 2207/20084* (2013.01); *G06T 2207/30024* (2013.01); *G06T 2207/30096* (2013.01)

(56) References Cited

U.S. PATENT DOCUMENTS

| | | | | |
|---|---|---|---|---|
| 11,094,058 | B2 * | 8/2021 | Buckler | .................... G06T 3/00 |
| 2018/0342058 | A1 | 11/2018 | Madabhushi et al. | |
| 2019/0371450 | A1 | 12/2019 | Lou et al. | |
| 2020/0184641 | A1 * | 6/2020 | Schmidt | .............. G06V 20/698 |
| 2020/0258223 | A1 * | 8/2020 | Yip | ......................... G06F 18/21 |
| 2021/0225511 | A1 * | 7/2021 | Kiraly | .................... G06N 20/20 |
| 2022/0301714 | A1 * | 9/2022 | Kim | ....................... A61B 6/032 |

OTHER PUBLICATIONS

Ren, K., Qin, J., Zheng, L., Yang, Z., Zhang, W., Qiu, L., & Yu, Y. (2018). Deep Recurrent Survival Analysis. arXiv.Org. (Year: 2018).*

Tabibu, S., Vinod, P. K., & Jawahar, C. V. (2019). Pan-Renal Cell Carcinoma classification and survival prediction from histopathology images using deep learning. Scientific Reports, 9(1), Article 10509. https://doi.org/10.1038/s41598-019-46718-3 (Year: 2019).*

Nie, D., Lu, J., Zhang, H., Adeli, E., Wang, J., Yu, Z., Liu, L., Wang, Q., Wu, J., & Shen, D. (2019). Multi-Channel 3D Deep Feature Learning for Survival Time Prediction of Brain Tumor Patients Using Multi-Modal Neuroimages. Scientific Reports, 9(1), 1103-1103. (Year: 2019).*

Mobadersany, P., Yousefi, S., Amgad, M., Gutman, D. A., Barnholtz-Sloan, J. S., Vega, J. E. V., Brat, D. J., & Cooper, L. A. D. ( 2018). Predicting cancer outcomes from histology and genomics using convolutional networks. Proceedings of the National Academy of Sciences—PNAS, 115(13), E2970-E2979. (Year: 2018).*

International Application No. PCT/US2021/040726 , "International Search Report and Written Opinion", Oct. 20, 2021, 10 pages.

European Application No. 21826556.9 , "Extended European Search Report", Jun. 3, 2024, 10 pages.

Nie et al., "Multi-Channel 3D Deep Feature Learning for Survival Time Prediction of Brain Tumor Patients Using Multi-Modal Neuroimages", Scientific Reports, vol. 9, No. 1, Jan. 31, 2019, 14 pages.

Srinidhi et al., "Deep Neural Network Models for Computational Histopathology: A Survey", Medical Image Analysis, vol. 67, Jan. 2021, 46 pages.

Wulczyn et al., "Deep Learning-based Survival Prediction for Multiple Cancer Types Using Histopathology Images", Available Online at: https://arxiv.org/pdf/1912.07354, Dec. 16, 2019, 28 pages.

* cited by examiner

LIHC, DLS, p=0.010

BLCA, DLS, p=0.153

SYSTEMS AND METHODS FOR DIRECTLY PREDICTING CANCER PATIENT SURVIVAL BASED ON HISTOPATHOLOGY IMAGES

CROSS-REFERENCE TO RELATED APPLICATIONS

This application claims priority to U.S. Provisional Patent Application No. 63/039,670, filed Jun. 16, 2020, titled Direct Cancer Patient Survival Prediction Using Histopathology Images, the entirety of which is hereby incorporated by reference.

FIELD

This disclosure generally relates to machine learning methods for predicting cancer patient survival from histopathology images, e.g., of a tumor biopsy obtained from the patient and imaged with a whole slide scanner

BACKGROUND

The ability to provide prognostic information in oncology can significantly impact clinical management decisions such as treatment and monitoring. One of the most common systems for this purpose is the American Joint Committee on Cancer (AJCC) "TNM" cancer staging system, whereby tumors are classified by primary tumor size/extent (T), lymph node involvement (N), and the presence or absence of distant metastasis (M). Although TNM staging is useful and well-studied, there is room for improvement in some settings, with ongoing efforts to develop improved prediction strategies that incorporate information such as clinical variables, genetic information, and histomorphological features including tumor grade.

SUMMARY

Various examples are described for systems and methods for directly predicting cancer patient survival based on histopathology images. One example method includes obtaining one or more histopathology images of a sample from a cancer patient; selecting a plurality of tissue image patches from the one or more histopathology images; determining, by a deep learning system comprising a plurality of trained machine learning ("ML") models, a plurality of image features for the plurality of tissue image patch, wherein each tissue image patch is analyzed by one of the trained ML models; determining, by the deep learning system, probabilities of patient survival based on the determined plurality of image features; and generating, by the deep learning system, a prediction of patient survival based on the determined probabilities.

One example weakly supervised deep learning system for prediction of prognosis of a cancer patient includes a non-transitory computer-readable medium; and a processor communicatively coupled to the non-transitory computer-readable medium, the processor configured to execute processor-executable instructions stored in the non-transitory computer-readable medium to obtain one or more histopathology images of a sample from a cancer patient; randomly select a plurality of tissue image patches from the one or more histopathology images; determine, by a deep learning system comprising a plurality of trained machine learning ("ML") models, a plurality of image features for the plurality of tissue image patch, wherein each tissue image patch is analyzed by one of the trained ML models; determine, by the deep learning system, probabilities of patient survival based on the determined plurality of image features; and generate, by the deep learning system, a prediction of patient survival based on the determined probabilities.

Another example weakly supervised deep learning system for prediction of prognosis of a cancer patient includes multiple convolutional neural networks modules with shared weights, wherein each of the multiple convolutional neural networks has as input one cropped tissue image patch randomly selected from a histopathology image, an average pool receiving the output of each of the convolutional neural networks and a fully connected layer, wherein each of the multiple convolutional neural networks extracting features from each patch, the patch level features averaged on a per-channel basis in the average pool and fed to the fully connected layer, the multiple convolutional neural networks trained from training images comprising at least one histopathology image from each of a multitude of cancer patients optionally across many different types of cancer patients to predict prognosis in accordance with a survival loss function as a probability distribution over discretized survival times, and wherein the deep learning system is trained without requiring the leveraging of expert annotations or known features of interest in the training images.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

DETAILED DESCRIPTION

Figure 1:
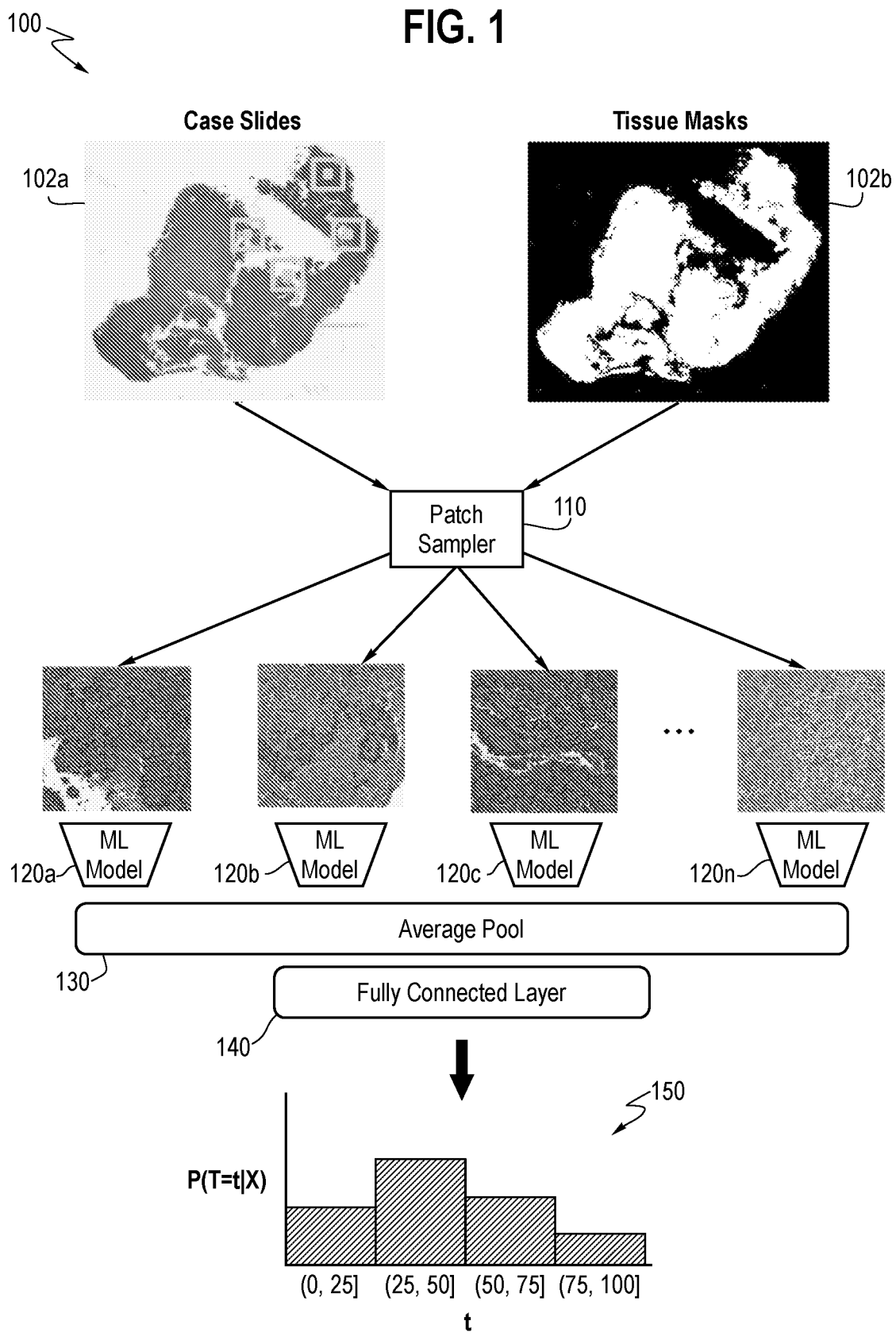
FIG. 1 shows an example deep learning system for directly predicting cancer patient survival based on histopathology images.

Examples are described herein in the context of systems and methods for directly predicting cancer patient survival based on histopathology images. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

In this document we build on and extend prior work by developing an end-to-end deep learning system to directly predict patient survival in multiple cancer types, training on whole-slide histopathology images and associated clinical data (including approximated diseases-specific survival) without leveraging expert annotations or known features of interest. An example of our deep learning system features a convolutional neural network that is directly optimized to extract prognostic features from raw image data, and an image subsampling method to tackle address images with large numbers of pixels, e.g., images with resolutions of 100,000×100,000 pixels. Several different loss functions can address the problem of right-censored patient outcomes.

We evaluated our example DLS's ability to improve risk stratification relative to the baseline information of TNM stage, age, and sex for ten cancer types from The Cancer Genome Atlas (TCGA). Though we observed improved risk stratification based on the model predictions for several cancer types, effect sizes were difficult to estimate precisely due to the limited number of cases and clinical events present in TCGA (350-1000 cases and 60-300 events per cancer type).

In one embodiment, a method is disclosed of predicting prognosis of a cancer patient from a set of one or more histopathology images of a sample from the cancer patient. The method includes the steps of: sampling at random cropped image patches from the set of one or more histopathology images; and supplying the one or more of the random cropped image patches to a deep learning system in the form of multiple convolutional neural networks modules with shared weights. The number of convolutional neural networks can vary depending on considerations such as processing speed and efficiency, and may include 10, 100 or even 1,000 or more networks. Each of the multiple convolutional neural networks has as input one of the random cropped image patches. The deep learning system is trained to predict prognosis from a set of training images in accordance with a survival loss function as a probability distribution over discretized survival times. The multiple convolutional neural networks are trained from training images in the form of at least one histopathology image from each of a multitude of cancer patients across many different types of cancer patients (e.g., 6, 8, 10 or 12 different types) and associated disease-specific survival data, and wherein the deep learning system is trained without requiring the leveraging of expert annotations or known features of interest in the training images. The method further includes the step of generating a prediction from the deep learning system, namely a prediction of survival time or placement in probability distribution over discretized survival times.

In one embodiment, the survival loss function is a censored cross-entropy function.

In one embodiment, the cancer patient has prostate cancer, breast cancer, colon cancer, head and neck squamous cell carcinoma, or liver hepatocellular carcinoma.

In another aspect, a weakly supervised deep learning system is disclosed for prediction of prognosis of a cancer patient. The deep learning system includes multiple convolutional neural networks modules with shared weights, wherein each of the multiple convolutional neural networks has as input one cropped tissue image patch randomly selected from a histopathology image, an average pool receiving the output of each of the convolutional neural networks and a fully connected layer, wherein each of the multiple convolutional neural networks extracting features from each patch, the patch level features averaged on a per-channel basis in the average pool and fed to the fully connected layer. The multiple convolutional neural networks are trained from training images comprising at least one histopathology image from each of a multitude of cancer patients, optionally across many different types of cancer patients, to predict prognosis in accordance with a survival loss function as a probability distribution over discretized survival times. The deep learning system is trained without requiring the leveraging of expert annotations or known features of interest in the training images.

In one possible configuration the system is further trained to make a prediction of a molecular characteristic in a tissue sample, for example presence of a genetic mutation. These mutations are both indicative of patient prognosis and used to make treatment decisions.

In another possible configuration the system is trained to make a prediction of whether the original tumor has metastasized away from the primary site, such as from the breast to the surrounding lymph nodes. Whether a cancer has metastasized is also prognostic and used in treatment decisions.

In one possible configuration, the multiple convolutional neural networks are trained from least one histopathology image from each of a multitude of cancer patients of a having a single type of cancer, e.g., breast cancer, or prostate cancer. Alternatively, the networks are trained from histopathology images across a variety of different cancer patients, such as breast, prostate, lung, and head and neck cancer patients.

In one further configuration, a system is contemplated in the form of a plurality of the weakly supervised deep learning system for prediction of prognosis of a cancer patient previously recited, such as 5 or 6 of such systems, wherein each of the plurality of weakly supervised deep learning systems is trained from least one histopathology image from each of a multitude of cancer patients of a having a single type of cancer, e.g., breast cancer, or prostate cancer.

The results reported here provide support for the feasibility of developing weakly supervised deep learning models to predict patient prognosis from whole-slide images across multiple cancer types.

Digitized whole-slide images of hematoxylin-and-eosin-(H&E-) stained specimens were obtained from TCGA and accessed via the Genomic Data Commons Data Portal (https://gdc.cancer.gov). Images from both diagnostic formalin-fixed paraffin-embedded (FFPE) slides and frozen specimens were included. Based on initial experiments as well as differences in the proportion of available FFPE images across cancer types (i.e. TCGA studies), both the FFPE and frozen whole-slide images (WSIs) available for each patient were used for training and case-level predictions. Each case contained 1-10 slides (median: 2). Clinical data (including approximated disease specific survival) is associated with each of the slides and were obtained from the TCGA Pan-Cancer Clinical Data Resource and the Genomic Data Commons.

Of the TCGA studies for which cancer stage data were available, we chose the ten studies with the highest number of cases and survival events. Clinical stage was used only for ovarian serous cystadenocarcinoma (OV), which did not have pathologic stage data available but was included given the high number of observed events. Cutaneous melanoma (SKCM) was excluded as it was not restricted to primary, untreated tumors. Thyroid carcinoma (THCA) was excluded because only 14 of 479 cases had an observed event. Cases with missing data for either pathologic stage, age, sex, or disease specific survival were excluded from evaluation, whereas only cases missing disease specific survival were excluded from model development (training and tuning).

For each TCGA study, cases were split into train, tune, and test sets in a 2:1:1 ratio. To ensure representative splits given the small number of cases, split assignment was further stratified on whether the time of disease specific survival event was observed, and the time-to-event (discretized into 3 intervals based on the $25^{th}$ and $75^{th}$ percentiles). Across all cancer types, 4,880 cases (12,095 images) were used for training and tuning. The remaining 1,216 cases (3,009 images) were used for evaluation. The pathologic stage distribution for each TCGA study and split is detailed in S1 Table.

The example deep learning system shown in FIG. 1 is trained on histopathology images that are obtained at a given magnification, typical for a given cancer type, e.g., 20×, or 10×.

A core element of our example deep learning system (DLS) included multiple convolutional neural network (CNN) modules with shared weights, and an average pooling layer that merges image features computed by these modules (see FIG. 1). For each case, cropped image patches were uniformly and randomly sampled from tissue-containing areas across all slides available for a given case. Next, image features were extracted for each patch by a convolutional neural network (CNN). These patch-level features were averaged (on a per-channel basis) and fed to a fully connected layer. Our custom loss function divided the follow-up period into four discrete bins depending on right-censorship time and outcome. As such, the model was designed to output a probability distribution over discretized survival times.

The output of the example DLS is a continuous risk score that can be used as a feature for survival analysis. To define low and high risk groups, cases were binned into risk quartiles using DLS risk scores (see for example the outputs shown in FIG. 1). Binning was done within each cancer type to ensure that the distribution of cancer types within each risk group was the same. A logrank test comparison between the Kaplan-Meier (KM) curves for the high and low risk groups yielded p<0.001 (see, e.g., FIGS. 4A-4D).

Given the known prognostic significance of stage, we assessed if the DLS could also sub-stratify patients' risk within each stage. The resulting Kaplan-Meier curves show that the DLS can further sub-stratify patients into low and high risk groups for stage II (p<0.05) and stage III cancers (p<0.001), but not for stage I or stage IV (see FIG. 3).

Next, we used multivariable Cox proportional-hazards regression to evaluate the significance of the DLS as a predictor of disease specific survival after adjusting for available variables: cancer stage, age, and sex. For the combined analysis including all 10 cancer types (i.e. "TCGA studies"), where cancer type was included as an indicator variable, the DLS was a significant predictor of 5-year DSS, with a hazard ratio of 1.48 (p<0.0001). To ensure that age and stage were adequately controlled for across studies, we further fit a combined model with additional interaction terms between the study and stage, and between study and age. In this expanded combined model, the p-value for the DLS remained below 0.001.

In sub-analysis of individual cancer types the DLS was significantly associated with disease specific survival for 5 of 10 cancer types, (Table 2; p=0.0002 to p=0.0257). Cancer stage was a significant predictor in 7 studies, while age and sex were each significant predictors in only one study each.

Although not available for all studies, we also conducted additional multivariable analysis to account for grade and histologic subtype when these data were present in sufficient quantity.

Finally, we also performed sub-analysis using only the FFPE (formalin fixed paraffin embedded) slides in the test set for evaluation. In this analysis using FFPE only slides, the hazard ratio of the DLS remained statistically significant for the combined analysis when analyzed across all studies (p<0.001), and for 3 individual cancer types in sub-analysis.

The concordance index (or c-index) assesses the goodness-of-fit for a survival model by calculating the probability of the model correctly ordering a (comparable) pair of cases in terms of their survival time. We compared the c-index of Cox-regression models with three different feature sets: (1) "DLS", consisting of the DLS predictions only; (2) "Baseline", consisting of stage, age, and sex; and (3) "Baseline+DLS", consisting of stage, age, sex, and DLS predictions. The c-index results for all cancer types combined and for each cancer type individually are summarized in Table 3. For the DLS model, the c-index for all 10 studies combined (comparisons across cases from different cancer types were excluded) was 61.1 (95% confidence interval (CI) [57.2, 65.1]). Within individual studies, the confidence intervals were too wide to draw meaningful conclusions due to low case volumes. We interpreted the delta in c-index between the "Baseline-only" and the "Baseline+DLS" models as a measure of the added predictive value of the DLS over the baseline variables. For all studies combined, the c-index delta was 3.7 (95% CI [1.0, 6.5]).

In addition to c-index, we also calculated the area under the receiver operating characteristic curve (AUC) for prediction of 5-year disease specific survival. Qualitatively similar results were observed, with the combined analysis showing an AUC improvement of 6.4 (95% CI [2.2, 10.8]).

Figure 4A:
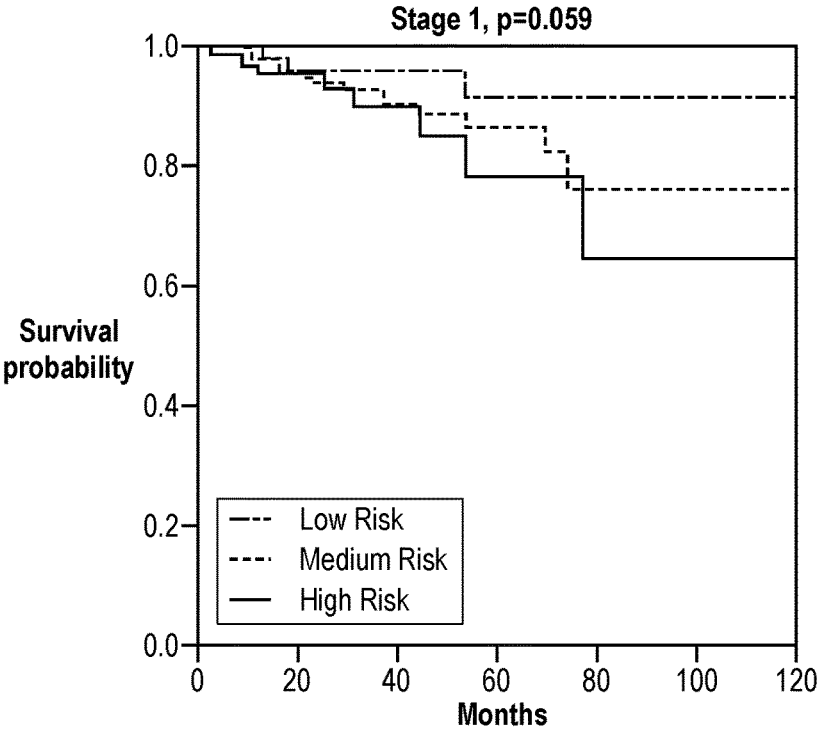
FIGS. 4A-4D are plots of Kaplan Meier curves for DLS risk groups within each cancer stage (stages 1-4, respectively).
Figure 4B:
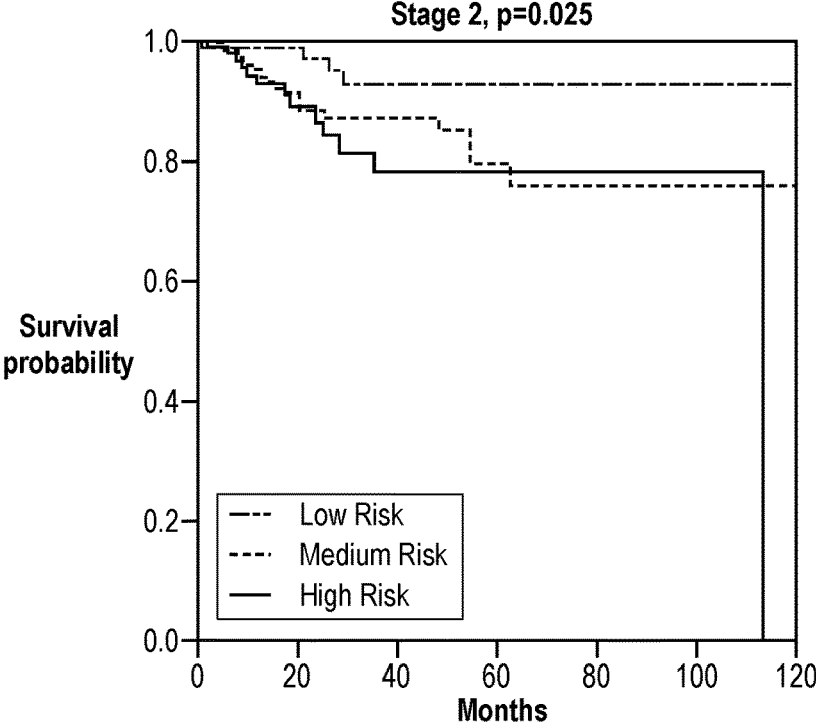
Figure 4C:
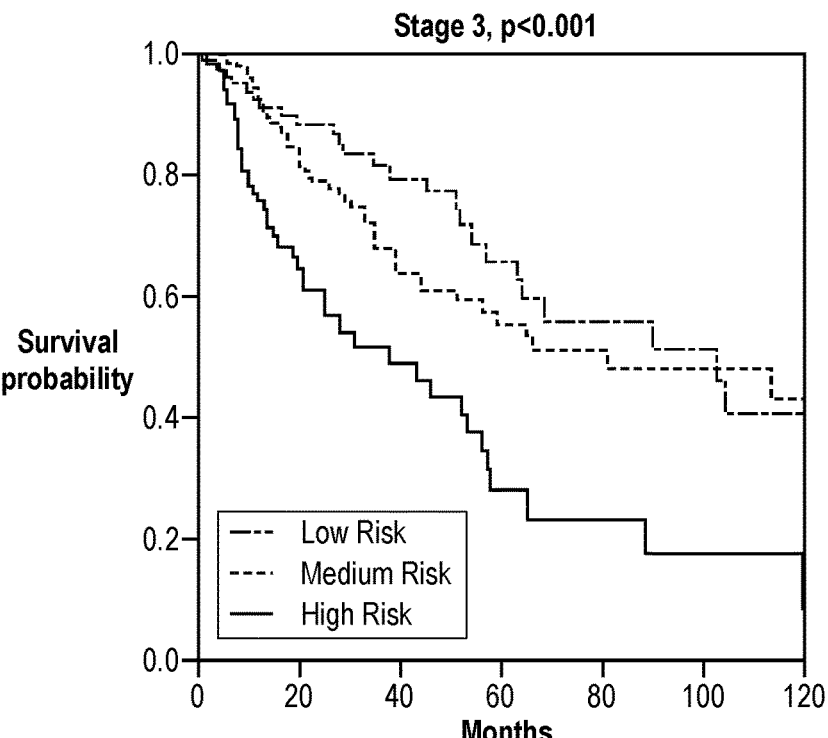
Figure 4D:
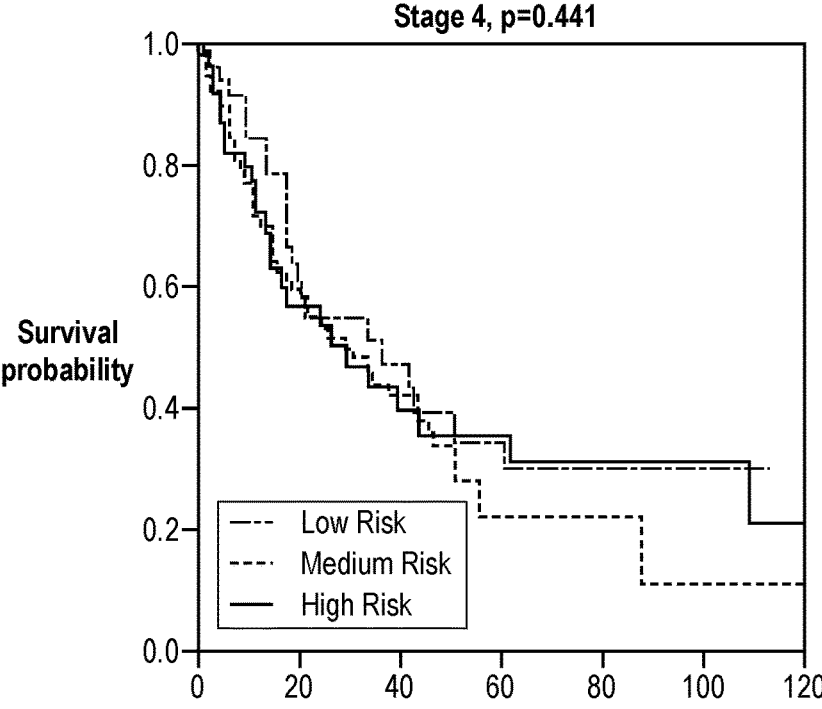

To gain initial insights into the DLS, we first computed the correlation of the DLS predictions with the baseline variables of stage, TNM categories, and age. The DLS predictions were not correlated with age in any study, but were correlated with stage and T-category in several cancer types as well as in the combined analysis. Next, we analyzed the regions of each slide that contributed to the overall case classification by extracting the individual patches with the highest and lowest patch-level DLS risk scores for further review. Using KIRC as a representative example with a consistently high-performing DLS model, the patches with the "most confident" predictions for high or low risk tended primarily to contain tumor (FIGS. 4A-4C), whereas patches with more intermediate prediction values tended to be non-tumor, such as fat, stroma, and fragmented tissue (FIG. 4D). In this analysis, more detailed associations of histologic features and patch-level risk predictions were not identified. Samples of high and low risk patches corresponding to the other cancer types for which the DLS provided significant prognostic value are provided in FIGS. 8-11.

Predicting patient prognosis in oncology underlies important clinical decisions regarding treatment and monitoring. In this work, we assessed the potential to improve predictions of disease-specific survival using a deep learning system trained without human annotations for known morphological features or regions of interest.

A natural question arises as to the value of developing algorithms to predict prognosis exclusively from machine learned features, versus leveraging region-level annotations for known features such as tumor grade, nuclear pleomorphism, tumor-infiltrating lymphocytes, or mitotic figures among others. One straightforward advantage is to avoid the cost, tediousness, and difficulties associated with region-level annotations. Furthermore, the relatively unbiased nature of these weakly supervised models potentially enables the learning of previously unknown or unappreciated prognostic features. The primary disadvantage, on the other hand, was the increased number of cases required to train accurate models given that there was only a single case-level training label for each image, such as survival or disease progression. To place the difficulty of this problem in context, these labels correspond to $10^9$ pixels per image, often with several images per case, making for significantly weaker supervision than in typical image prediction tasks that deal with images sized $10^5$-$10^6$ pixels. In addition, cancer survival prediction is by nature limited to several orders of magnitude less data than typical image classification problems (e.g. $10^5$-$10^6$ images for ImageNet versus $10^2$-$10^3$ images here).

An example DLS according to this disclosure learned morphologic features that were predictive of disease-specific survival in multiple cancer types. While we did not identify any clear trends or confounders specific to the cancer types for which the models performed best, future work to better understand the effects of sample size, image-specific variables, and disease-specific variables on clinical predictions from WSIs will be important for the field. Our solution for weak supervision involves a neural network architecture that randomly samples multiple tissue-containing patches for each case at training time. This sampling approach has three main advantages. First, it provides a high probability of seeing patches containing informative features in each training iteration, and even more so across training iterations. Second, assuming each case contains more than one informative image patch, it substantially expands the effective dataset size by increasing the diversity of examples. Third, even uninformative patches have a regularization effect on the training.

An example DLS, in one example, output remained significantly associated with disease specific survival even after adjusting for age and cancer stage suggests that the DLS learned prognostic morphologic features that were independent from these baseline variables. In an effort to better understand some of the learned features, we applied the DLS to every image patch on each slide to obtain "patch-level prognosis estimates" across the entire image. In this analysis, the most confident prognostic regions were comprised primarily of tumor with minimal intervening stroma or other obvious histological structures. While other machine learning efforts have identified prognostic significance for non-tumor elements, our observations suggest that at least for our specific models, the morphologic features of the tumor appear to be more relevant than non-tumor regions. However, elucidating the morphological features that the DLS learned to help distinguish between high risk and low risk cases remains an exciting but challenging topic for future efforts, and one that will likely require identification of unique features for different tumor types. One intriguing hypothesis is that DLS-learned features may correspond to previously unappreciated representations of tumor biology in the histology, and that underlying biological pathways or molecular mechanisms may be further elucidated via focused evaluation of regions highlighted by the DLS.

Providing prognostic information at the time of cancer diagnosis has important implications for treatment and monitoring. Although cancer staging, histopathological assessment, molecular features, and clinical variables can provide useful prognostic insights, improving risk stratification remains an active research area. We developed a deep learning system (DLS) to predict disease specific survival across ten cancer types from The Cancer Genome Atlas (TCGA). We used a weakly-supervised approach without pixel-level annotations, and tested three different survival loss functions. An example DLS according to this disclosure was developed using 9,086 slides from 3,664 cases and evaluated using 3,009 slides from 1,216 cases. In multivariable Cox regression analysis of the combined cohort including all ten cancers, the DLS was significantly associated with disease specific survival (hazard ratio of 1.58, 95% CI 1.28-1.70, p<0.0001) after adjusting for cancer type, stage, age, and sex. In a per-cancer adjusted subanalysis, the DLS remained a significant predictor of survival in 5 of 10 cancer types. Compared to a baseline model including stage, age, and sex, the c-index of the model demonstrated an absolute 3.7% improvement (95% CI 1.0-6.5) in the combined cohort. Additionally, our models stratified patients within individual cancer stages, particularly stage II (p=0.025) and stage III (p<0.001).

By developing and evaluating prognostic models across multiple cancer types, this work represents one of the most comprehensive studies exploring the direct prediction of clinical outcomes using deep learning and histopathology images. Our analysis demonstrates the potential for this approach to provide significant prognostic information in multiple cancer types, and even within specific pathologic stages.

Referring now to FIG. 1, FIG. 1 is a diagram showing a deep learning system ("DLS") 100 for directly predicting cancer patient survival based on histopathology images. This example system 100 includes a patch sampler 110 which is communicatively coupled to the inputs of multiple trained machine learning ("ML") models 120a-n. Any suitable number of ML models may be used, e.g., anywhere from 1 to 1024 ML models in some examples, though more than 1024 ML models may be employed. The outputs of the ML models 120a-n are communicatively connected to an averaging pool 130, which accepts image features determined by the ML models and merges them. The output of the averaging pool 130 is communicatively connected to a fully connected layer 140, which generates a distribution of probabilities sorted into discrete bins.

In operation, the patch sampler 110 receives one or more one or more histopathology images of a sample from a cancer patient and randomly samples image patches from the histopathology image(s). In this example, the sampled image patches are uniformly sized, though, in some examples, the sizes may vary between patches. The patch sampler 110 in this example generates patches of 256 pixels by 256 pixels, though any suitable patch size may be employed. In addition, the patch sampler 110 may apply a mask to a histopathology image to remove non-tissue regions from the respective image, which may affect the number of image patches extracted from a single histopathology image. Though in some examples, a mask may be applied by the ML models 120a-n. The patch sampler 110 then aggregates the various image patches and supplies them randomly to the various ML models 120a-n for processing. In this example, each ML model 120a-n receives one or more image patches, depending on the number of image patches generated by the patch sampler from the one or more histopathology images. However, no ML model 120a-n receives the same image patch, though in some examples, multiple ML models 120a-n may receive the same image patch.

Each ML model 120a-n receives image patches from the patch sampler 110 and extracts image features, which are then output to the averaging pool 130. In this example, the ML models 120a-n are convolutional neural networks ("CNN"); however, any suitable ML models may be employed according to different examples, such as a residual neural network ("Resnet") or NASNET provided by GOOGLE LLC from MOUNTAIN VIEW, CALIFORNIA, or a recurrent neural network, e.g. long short-term memory ("LSTM") models or gated recurrent units ("GRUs") models. The ML models 120a-n can also be a three-dimensional CNN ("3DCNN"), a dynamic time warping ("DTW") technique, a hidden Markov model ("HMM"), etc., or combinations of one or more of such techniques—e.g., CNN-HMM or MCNN (Multi-Scale Convolutional Neural Network). Further, some examples may employ adversarial networks, such as generative adversarial networks ("GANs"), or may employ autoencoders ("AEs") in conjunction with ML models, such as AEGANs or variational AEGANs ("VAEGANs").

As discussed above, the ML models 120a-n in this example are CNNs. Each CNN module includes depth-wise separable convolution layers, similar to the MobileNet CNN architecture. The layer sizes and the number of layers in these example CNNs were tuned via a random grid-search:

| Hyperparameter | Description | Possible values |
| --- | --- | --- |
| Fixation Types | Fixation types for slides for both training and evaluation | FFPE, "FFPE and FROZEN" |
| Patch size | Height and width of each image patch | 256 |
| Patch set size | Number of patches sampled from a case to form a single training example: | 1, 4, 8, 16 |
| Magnification | Image magnification at which the patches are extracted | 20X, 10X, 5X |
| Number of layers | Number of layers used | 4, 8, 12 (i.e., "stride_1_layers" is 0, 1, or 2; see pseudocode below) |

-continued

| Hyperparameter | Description | Possible values |
| --- | --- | --- |
| Base depth | Depth of the first convolution layer in the MobileNet CNN; depth grows by a factor of 1.25 for every 2 layers in the network. | 8, 16 |
| L2 regularization weight | Weight of the L2 loss used for regularization | 0.004, 0.0004, 0.00004, 0.000004 |
| Initial Learning rate | Initial learning rate used for the RMSPROP optimizer; decay rate was 0.99 every 20,000 steps. | 0.005, 0.001, 0.0005, 0.0001 |
| Thresholds | Percentile thresholds used for binning time in the censored cross-entropy loss. | [50], [25, 75], [25, 50, 75] |
| Training dataset | Trained on study (cancer-type) specific data, or combined across all cancers | Combined or cancer-specific |

However, it should be appreciated that while these hyperparameters and corresponding values were used according to these examples, different values may be employed according to other examples. For example, image patch sizes may be of any suitable sizes, including 128-pixel, 512-pixel, 1024-pixel, etc., or patch sizes may be determined based on a total image size and dividing by a number of desired image patches, e.g., per row and column. Similarly, other hyperparameters may be adjusted according to systemic constraints or design goals.

The following example pseudocode may provide CNN definition for some examples and may be adjusted as discussed above:

```
// Depth of the first convolution layer (tuned)
base_depth := 16
// Rate of depth growth with every stride 2 layer (fixed)
depth_growth := 1.25
// Num stride 2 layers (fixed)
stride_2_layers := 4
// Num stride 1 layers per stride 2 layer (tuned)
stride_1_layers := 1
// Size of convolution kernel (fixed)
kernel_size := 3
features = Conv2D(images, base_depth, kernel_size, stride=1)
for i := 1 to stride_2_layers do
  depth = int( base_depth * depth_growth ** i )
// DepthwiseSeparableConv 2D is available as
tf.keras.layers.SeparableConv2D
features = DepthwiseSeparableConv 2D( features, depth, kernel_size,
stride=2)
for j := 1 to stride_1_layers do
  features = DepthwiseSeparableConv 2D( features, depth,
kernel_size, stride=1)
features = AveragePooling2D(features)
```

In this example, each of the CNNs is the same and they all share weights. Thus, any number of CNNs may be employed in different examples. As discussed above, each CNN 120a-n takes as input a randomly selected image patch from the one or more images for each patient, such that when multiple patches were sampled, probabilistically at least one patch was likely to be informative of the outcome. Specifically, if the frequency of informative patches on a slide is p, the probability of not sampling any informative patch in n patches decays exponentially with $n{:}(1{-}p)^n$, shrinking towards zero with even moderate values of n. This approach thus handles the weak label nature of survival prediction on large images, where the location of the informative region in the image or set of images is unknown. Furthermore, this approach naturally generalizes to multiple slides per case. During each training iteration, the n patches were sampled randomly, further ensuring that informative patches were sampled across training iterations.

In this example, each image patch is 256×256 pixels and was sampled uniformly at random from tissue-containing regions within all histopathology images for a particular patient. The tissue masks were created and applied to the case slides as shown in FIG. 1 in order to isolate the tissue containing regions and designate patches for training. The CNNs 120a-n then extracted image-based features from the patches. A top-level average-pooling layer allowed the model to take as input different number of patches between training and evaluation. This enabled the use of a smaller number of patches and resultant higher case diversity during training, and a more extensive coverage of slides in each case with a larger number of patches during evaluation. A final logistic regression layer produced a prediction given the output of the average pooling layer. And while CNNs were used in this example, any suitable ML model type may be employed, as discussed above.

The averaging pool 130 receives image features from the ML models 120a-n and, for each image feature channel, averages the image feature values in that channel. Thus, if the ML models 120a-n output sets of four image features $(F_1, F_2, F_3, F_4)$, the values for $F_1$ (an image feature channel) from all ML models are averaged separately from the values for $F_2$-$F_4$, and so forth. Depending on the types of ML models 120a-n, the training employed for each, the type of cancer in the histopathology images, etc., different numbers and types of features may be identified. However, the averaging pool 130 may average for each feature channel of whatever feature channels are output by the ML models 120a-n. The averaging pool 130 then supplies the averaged feature values to the fully connected layer 140.

The fully connected layer 140 in this example receives the averaged patch-level features (per channel). The fully connected layer 140 then employs a loss function to determining probabilities of patient survival across a number of discrete buckets. In this example, the loss function employs four buckets, representing probability intervals of (1) 0-25%, (2) 25-50%, (3) 50-75%, and (4), 75-100%, as can be seen in FIG. 1, which map to expected survival times based on statistical survival times for patients with the particular type of cancer, e.g., 0th to 25th percentile in bucket (1) above. However, any suitable bucketing scheme may be employed.

The DLS 100 was initially trained using censored cross-entropy, which is an extension of the standard cross-entropy loss used for classification models to train survival prediction models with right-censored data. We modeled survival prediction as a classification problem instead of a regression or ranking problem, by discretizing time into intervals and training models to predict the discrete time interval in which the event occurred instead of a continuous event time or risk score. For examples with observed events, the standard cross-entropy was computed. However for censored examples, the time interval in which the event occurs is unknown. Therefore, we leverage the information that the event did not occur before the censorship time and maximize the log-likelihood of the event occurring in the interval of censorship or thereafter. The full loss function can be written as follows:

$$\max \sum_i \left( O_i * \log(f(X_i)[Y_i]) + (1 - O_i) * \log\left( \sum_{y > Z_i} f(X_i)[y] \right) \right)$$

Where $Y_i$ is the interval in which the event occurred (for example with observed events) and $Z_i$ is the latest interval whose endpoint is before the time of censorship (for censored examples). f(x) is a predicted probability distribution over time intervals and f(x)[y] is the probability assigned by the model for the event occurring in the $y_{th}$ interval. One design consideration when using this loss function is how to discretize time. We used different percentiles of the time to death distribution for non-censored cases (e.g., quartiles). Discretization was done separately for each study to account for the considerable differences in survival times across studies (cancer types). To obtain a scalar risk score for evaluation, we took the negative of the expectation over the predicted time interval likelihood distribution. The negation ensured that higher risk score values indicate higher risk. And while a censored cross-entropy technique was used in this example, other types of training methodologies may be used in some examples.

For example, a loss function based on the Cox partial likelihood, which is used for fitting Cox proportional hazard models but be extended to train neural networks as follows:

$$\max \prod_{i:O_i=1} \frac{e^{f(X_i)}}{\sum_{j:T_j \geq T_i} e^{f(X_j)}}$$

Where $T_i$ is the event time or time of last follow-up, $O_i$ is an indicator variable for whether the event is observed, $X_i$ is the set of whole slide images and $f(X_i)$ is the DLS risk score, each for the $i^{th}$ case. In one such example, Breslow's approximation for handling tied event times may be employed. In principle, the loss for every single example is a function of all cases in the training data. In practice, the loss at each optimization step may be approximated by evaluating it over the examples in a small batch (n≤128) instead of the entire training dataset.

In another example, a loss function may be an exponential lower bound on the concordance index. The concordance index is a performance metric for survival models that corresponds to the probability that a randomly chosen pair of subjects is correctly ordered by the model in terms of event times. The concordance index itself is not differentiable, however, Raykar et al. (Steck H, Krishnapuram B, Dehing-oberije C, Lambin P, Raykar V C. On Ranking in Survival Analysis: Bounds on the Concordance Index. In: Platt J C, Koller D, Singer Y, Roweis S T, editors. Advances in Neural Information Processing Systems 20. Curran Associates, Inc.; 2008. pp. 1209-1216) proposed the following differential lower bound that can be used for model optimization:

$$E := \{(i, j) \mid O_i = 1 \text{ and } T_j > T_i\}$$
$$\max \sum_{(i,j) \in E} 1 - e^{f(X_i)-f(X_j)}$$

Where E is the set pairs of examples (i, j) where the $i^{th}$ event is observed and $T_j > T_i$. Similar to the Cox partial likelihood, we approximated this lower bound on the concordance index at each optimization step by evaluating it over the examples in a small batch (n≤128) instead of the entire training dataset. And while these examples additional loss functions may be suitable in some examples, other types of loss functions may be employed according to other examples.

In this example, training examples consisted of sets of up to 16 image patches per case sampled uniformly from tissue across all the slides in that case. Tissue detection using a pixel-intensity-based threshold as well as data augmentation via stain normalization followed by color and orientation perturbations were both performed as described previously. Training was performed using WSIs (whole slide images) for both frozen and FFPE specimens. Numerical optimization of network parameters was done using the RMSProp optimizer in TensorFlow in a distributed fashion, using 10 worker machines with 16 processors each. For each study, the hyperparameters were tuned by randomly sampling 50 hyperparameter configurations and then training one model with each configuration for each of the 10 studies (500 models in total).

At evaluation of the DLS 100, 1024 patches per case were sampled, using the same procedure as during training using the DLS shown in FIG. 1 and multiple CNNs (in this case 1,024) each operating on different image patches. The final models used for evaluation were averaged in a number of ways. First, model weights were the exponential moving average of model weights across training steps, with a decay constant of 0.999. Next, instead of picking a single best training checkpoint (i.e. a model evaluated at a particular training step) for each study, we used an ensemble of 50 checkpoints. Each model was trained for 500,000 steps and evaluated every 25,000 training steps, yielding 20 checkpoints per model, and a total of 1,000 checkpoints across 50 hyperparameter settings. The 50 checkpoints that achieved the highest c-index on the tune set were selected for the ensemble. The final ensemble prediction was the median of the 50 individual predictions It should be appreciated that the DLS 100 illustrated in FIG. 1 may be specifically trained to predict patient survival for a particular type of cancer or tumor. In some examples, a system for directly predicting cancer patient survival based on histopathology images may employ multiple DLSes 100, each trained on a different cancer type. Alternatively, in some examples, one DLS 100 may be trained on multiple different cancer types. Further, some systems may employ combinations of DLSes that are trained on a single type of cancer and those trained on multiple types of cancer. In another possible embodiment the example DLS of FIG. 1 is developed and trained from training images across cancer types, for example across multiple cancer types (e.g., bladder urothelial carcinoma, breast invasive carcinoma, colon adenocarcinoma, head and neck squamous cell carcinoma, kidney renal clear cell carcinoma, liver hepatocellular carcinoma, lung adenocarcinoma, lung squamous cell carcinoma, ovarian serous cystadenocarcinoma, stomach adenocarcinoma) in order to learn shared features which are common across multiple cancer types. This may particularly be the case where the number of training images for a given cancer types is relatively low, and by combining training images across multiple types of cancer a larger set of training data is available. At the time of use (inference on a previously unseen set of images) of a given cancer type, e.g., breast cancer tissue image, the associated breast cancer may then be model used to generate the risk score.

After the fully connected layer 140 processes the received input from the averaging pool 130, it outputs probabilities as discussed above. A risk score can be generated as an output of the fully connected layer.

The output of the DLS, in this example, is a continuous risk score that can be used as a feature for survival analysis. To define low and high risk groups, cases may be binned into risk quartiles using DLS risk scores (see for example the outputs shown in FIG. 1). Binning was done within each cancer type to ensure that the distribution of cancer types within each risk group was the same. A logrank test comparison between the Kaplan-Meier (KM) curves for the high and low risk groups yielded p<0.001 (see, e.g., FIGS. 3A-3D). In one embodiment the risk score can take the form of four numbers, each reflecting a probability of the associated tissue image being placed in each of the four survival risk bins shown in FIG. 1.

In one example, after generating the probability bins, the system may determine a single risk score based on the respective probabilities. For example, the deep learning system 100 may select the bin with the highest probability as the risk score for the patient. However, in some examples, the system may determine a difference between the highest probability bin and the next highest probability bin and, if the difference exceeds a threshold, it may output the highest probability bin as the risk score (e.g., $25^{th}$-$50^{th}$ percentile). Otherwise, it may output the two highest probability bins. Still other approaches to outputting a risk score may be employed according to other examples.

In some examples, risk heatmaps for patch analysis were generated by running the DLS on a single patch at a time to produce patch-level DLS risk scores across entire slides. To generate visualizations for pathologist review, patches were sampled based on patch-level risk score from the top 25% and bottom 25% from each case. Patches were grouped by case and cases were organized by patient-level risk prediction. These organized patches were then reviewed by two pathologists to qualitatively evaluate high-level features that may be associated with both the case-level and patch-level risk scores In some examples, the example DLS shown in FIG. 1 may be used to further train the DLS to predict molecular characteristics of cancer samples, for example the presence of genetic mutations which are relevant to cancer prognosis, survival and/or treatment. Molecular tests to determine such characteristics can be clinically useful, but have several limitations, including cost ($3,000+ for GEP tests or sequencing panels), access/resources (sometimes access to laboratories that can run and interpret such tests is difficult or impossible), and turnaround time (can be 2-4 weeks; therapy initiated before results are returned). The example DLS can accomplish two objectives: 1) predict biomarkers (ex. mutations, signatures, GEP, TMB, HRD) and (2) using molecular features as auxiliary inputs to improve diagnostic/prognostic predictions. The DLS system of FIG. 1 uses the weakly supervised learning methodology with case-level labels only (i.e., without expert level patch annotation or feature generation). For colon cancer specimens we were able to make the following predictions for genetic mutations in the chart below:

| $n_{validation}$ = 109 | AUC | CI (bootstrapped 95%) | $n_{positive}$ |
|---|---|---|---|
| KRAS | 0.760 | 0.683-0.836 | 37 |
| *RAS | 0.772 | 0.696-0.846 | 44 |
| TP53 | 0.806 | 0.736-0.871 | 50 |
| APC | 0.783 | 0.710-0.850 | 65 |
| BRAF | 0.842 | 0.757-0.916 | 11 |

For lung cancer we were able to make predictions of the following mutations:

| $n_{validation}$ = 127 | AUC | CI (bootstrapped 95%) | $n_{positive}$ |
|---|---|---|---|
| TP53 | 0.681 | 0.597-0.762 | 66 |
| EGFR | 0.757 | 0.653-0.858 | 22 |
| KEAP1 | 0.723 | 0.617-0.825 | 27 |
| KRAS | 0.712 | 0.616-0.799 | 30 |
| STK11 | 0.698 | — | — |
| NF1 | 0.818 | 0.725-0.905 | 17 |

For prostate cancer, we were able to make the following mutation predictions:

| $n_{validation}$ = 96 | AUC | CI (bootstrapped 95%) | $n_{positive}$ |
|---|---|---|---|
| SPOP | 0.793 | 0.666-0.912 | 9 |
| TP53 | 0.665 | 0.525-0.796 | 19 |
| FOXA1 | — | — | 4 |
| BRAF | — | — | 1 |

For breast cancer we were able to make the following mutation predictions:

| nvalidation = 151 | AUC* | CI (bootstrapped 95%) | $n_{positive}$ |
|---|---|---|---|
| ER | 0.86 | [0.830-0.925] | 115 |
| PR | 0.73 | [0.679-0.812] | 98 |
| HER2 | 0.72 | [0.641-0.816] | 22 |
| PIK3CA | 0.81 | [0.772-0.874] | — |
| TP53 | 0.82 | [0.784-0.879] | — |
| GATA3 | 0.66 | [0.601-0.759] | — |
| MAP3K1 | 0.68 | [0.622-0.803] | — |

The presence of certain mutations can indicate that patients may not respond to certain drugs or combinations of drugs in treatment of the cancer. Hence, predictions of the mutation state of the patient can lead directly to predictions of treatment response (or lack of response). Accordingly, the predictions of mutation state, in combination with known and published research regarding treatment response and dependency on mutation state allows the DLS to make predictions of treatment response.

Figure 2:
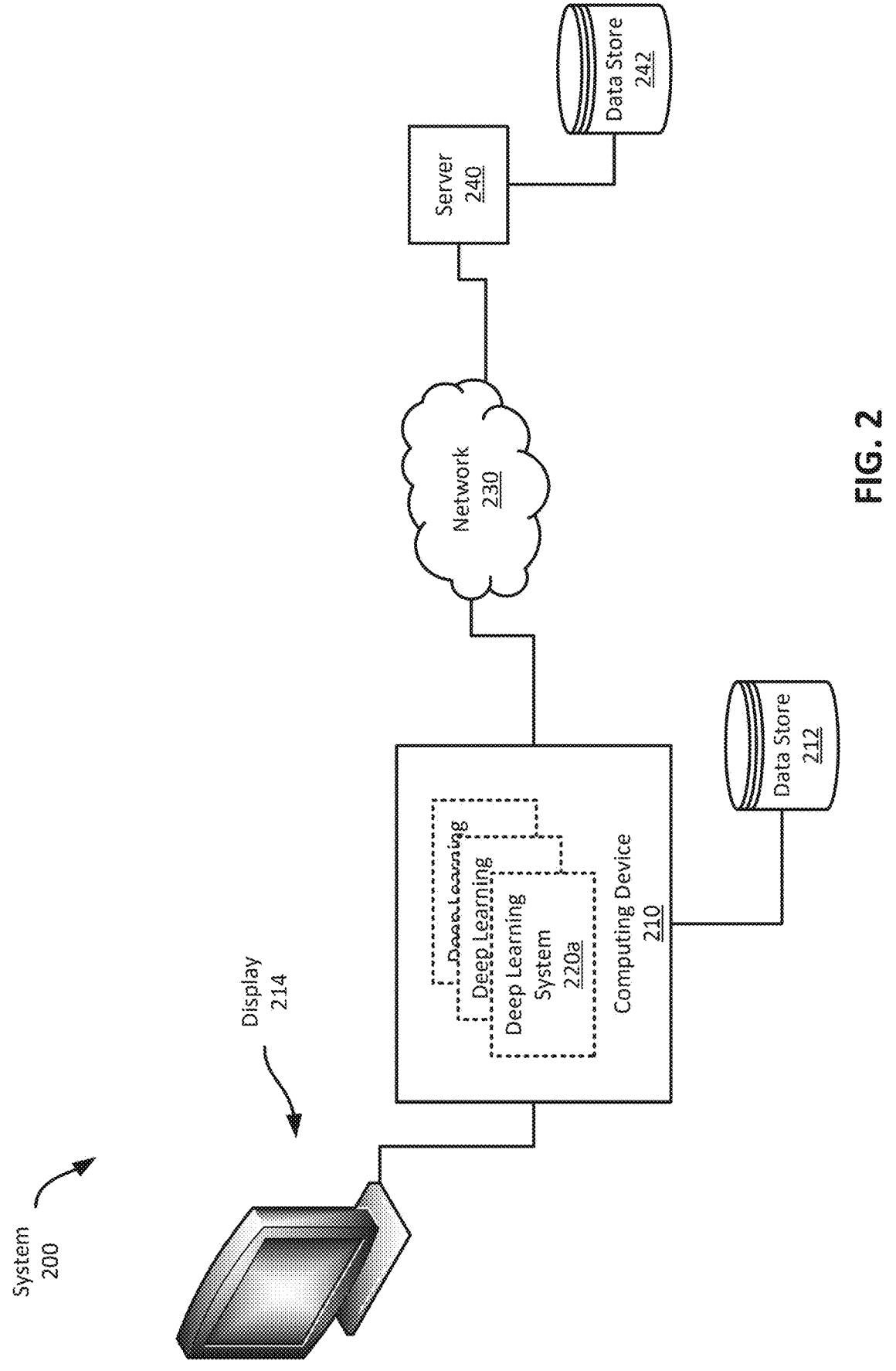
FIG. 2 shows an example system for directly predicting cancer patient survival based on histopathology images.

A two stage model approach is contemplated in which the ML models 120a-n of the DLS are used in a first stage to generate features from the whole-slide images (mitosis, granular, tubule formation etc.) and those features along with case metadata are supplied to a second neural network model which generates an output of molecular prediction. Additionally, the architecture of FIG. 1 can be further trained to predict cancer spread beyond the local tumor environment, for example distant metastasis to lymph nodes or other tissue in breast cancer patients Referring now to FIG. 2, FIG. 2 shows an example system 200 for directly predicting cancer patient survival based on histopathology images. The example system 200 includes a computing device 210 that has access to a data store 212 and is connected to server 240 and its data store 242 via network 230. In this example, the computing device 210 accesses digitized histopathology images from data store 212 and provides them to the one or more DLSes 220a-n for analysis, such as using the system 100 described above with respect to FIG. 1. After completing the analysis, the DLS(es) 220a-n provides to the computing device 210, stores them in data store 222 for later retrieval, e.g., by medical personnel, or displays them on the display 214.

While in this example, the computing device 210 receives the histopathology images from its own data store 212, in some examples, it may obtain histopathology images from the server 240, which may access its own data store 242 to obtain and provide requested histopathology images. Further, while the analysis is performed by DLSes 220a-n executed by the computing device 210 itself, in some examples, the DLSes 220a-n may be part of the server 240, and the computing device 210 may provide histopathology images to the server 240for analysis, via network 230, and later receive the results, which may be stored in the data store 212 or displayed on the display 214.

In this example, the server 220 is maintained by a medical provider, e.g., a hospital or laboratory, while the computing device 210 is resident at a medical office, e.g., in a pathologist's office. Thus, such a system 200 may enable medical providers at remote locations to obtain predictions for cancer patient survival, even if they lack the trained DLSes. However, it should be appreciated that example systems according to this disclosure may only include computing device 210, which may perform the analysis itself without communicating with a remote computing device.

To implement systems according to this example system 200, any suitable computing device may be employed for computing device 210 or server 220. Further, while the computing device 210 in this example accesses digitized histopathology images from the data store 212, in some examples, the computing device 210 may be in communication with an imaging device that captures images of pathology samples. Such a configuration may enable the computing device to capture one or more images of a pathology sample and immediately process it using suitable DLSes 220a-n, or provide it to a remote computing device, e.g., server 240, for analysis.

Figure 3:
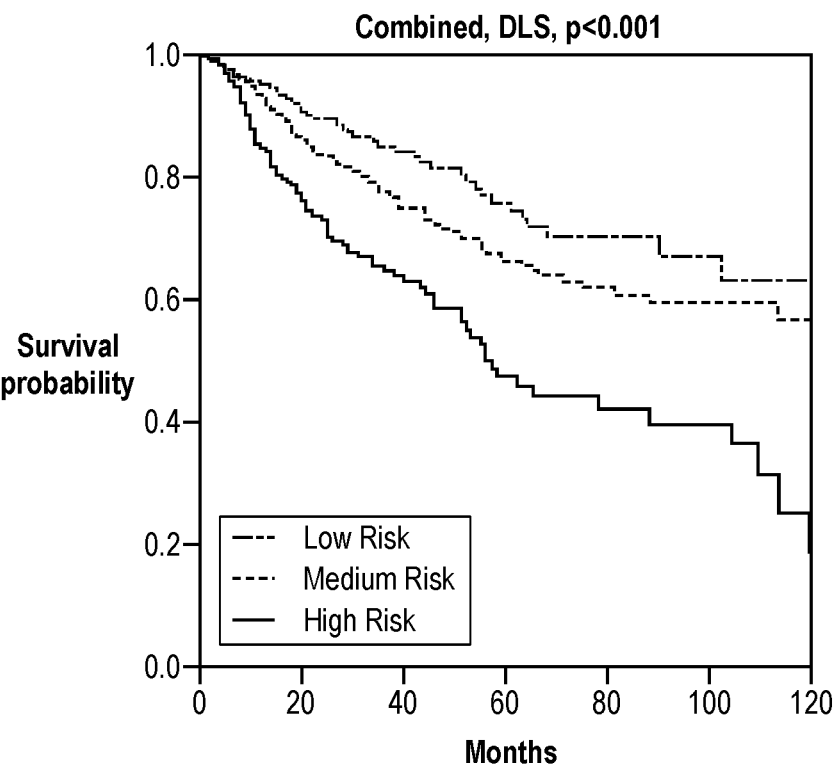
FIG. 3 is a plot of Kaplan Meier curves for DLS risk groups.

Referring now to FIG. 3, FIG. 3 is a plot of Kaplan Meier curves for DLS risk groups. To define low and high risk groups, cases were binned into risk quartiles using DLS risk scores. Binning was done within each cancer type to ensure that the distribution of cancer types within each risk group was the same. Different line conventions represent the different risk groups: one for the low risk ($0^{th}$-$25^{th}$ percentile); one for medium risk ($25^{th}$-$75^{th}$ percentile), and another for high risk ($75^{th}$-$100^{th}$ percentile). P-values were calculated using the binary logrank test comparing the low and high risk groups. The Kaplan Meier curve for each individual cancer type is shown in the collection of plots in FIGS. 4A-4D, 5A-5D, and 7A-7J.

FIGS. 4A-4D are plots of Kaplan Meier curves for DLS risk groups within each cancer stage (stages 1-4, respectively). To define low and high risk groups, cases were binned into risk quartiles using DLS risk scores. Binning was done within each stage and cancer type. This ensures that for each stage, the distribution of cancer types within each risk group was the same. P-values were calculated using the binary logrank test comparing the low and high risk groups. Unfortunately, there were insufficient cases and events to meaningfully perform this analysis stratified by cancer type in addition to stage.

Figure 5A:
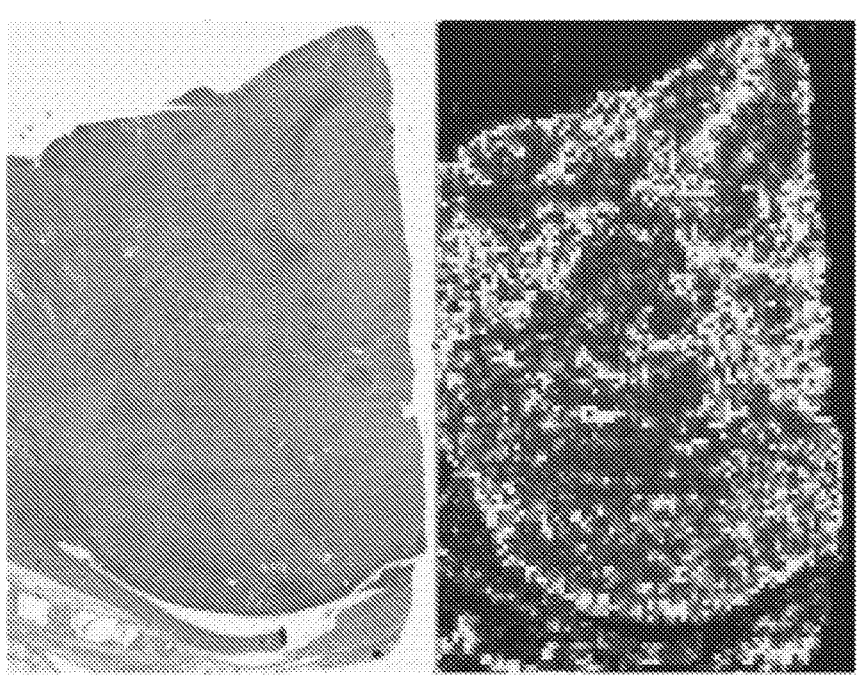
FIGS. 5A-5D consists of visualization of four groups (A, B, C and D) of image patches influencing survival prediction.
Figure 5B:
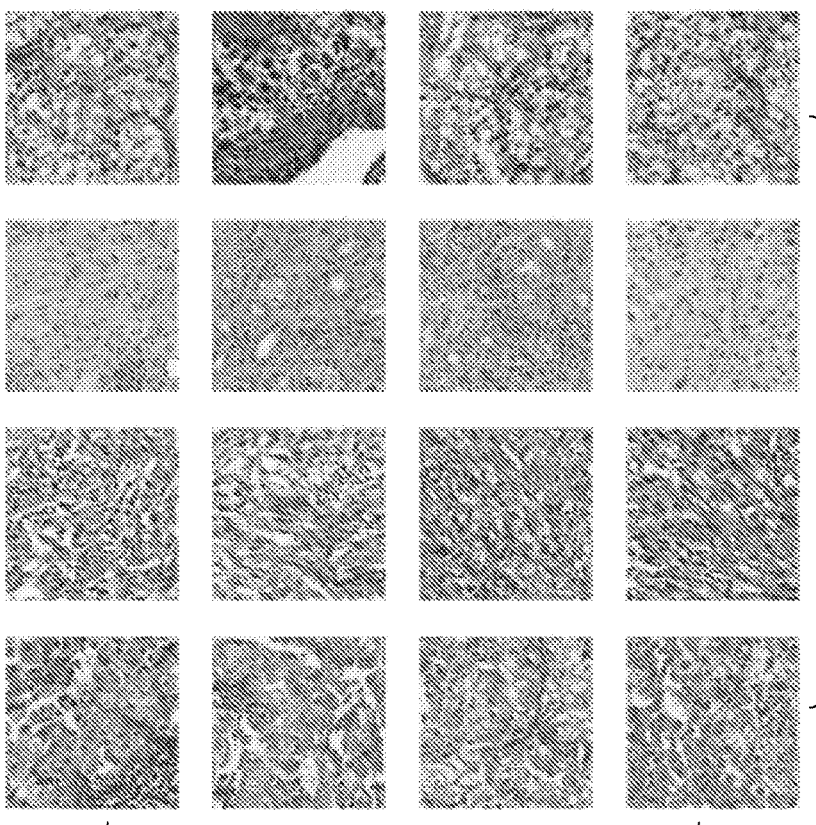
Figure 5C:
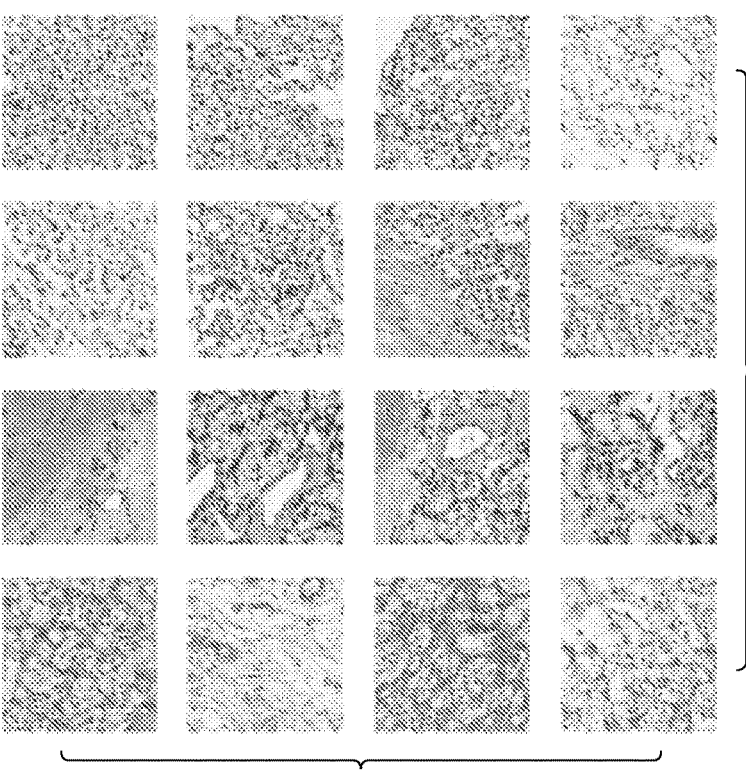
Figure 5D:
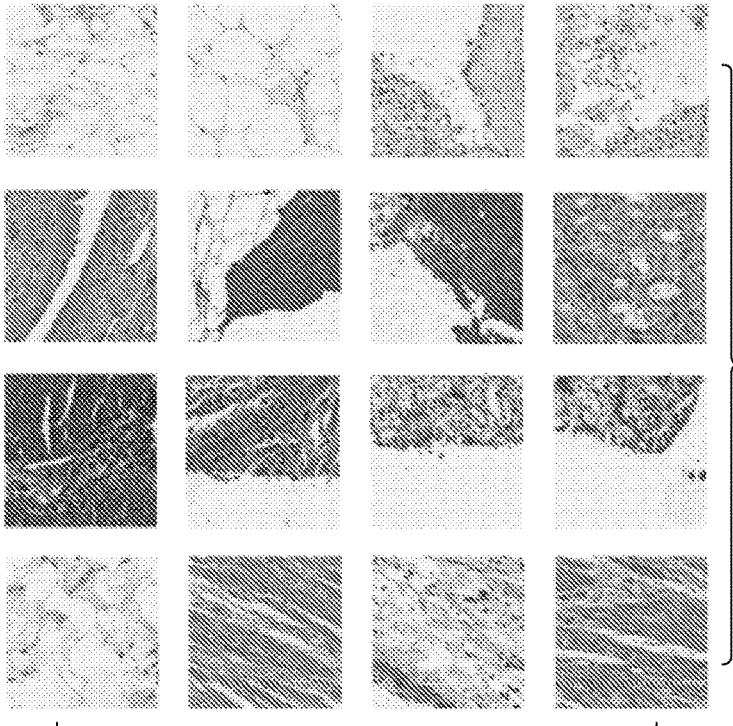

FIGS. 5A-5D consists of visualization of four groups (A, B, C and D) of image patches influencing survival prediction. FIG. 5A: Example of WSI kidney renal clear cell carcinoma (KIRC) predicted to be high risk (left), with the DLS-predicted "risk heatmap" on the right; darker patches within the tissue correspond to "high-risk" and lighter patches to "low-risk" patch-level predictions. FIG. 5B: "Highest-risk" patches from cases predicted to be high-risk. FIG. 5C: "Lowest-risk" patches from cases predicted to be low-risk. FIG. 5D: "Lowest-risk" patches from cases predicted to be high-risk. For FIGS. 5B, 5C, and 5D, patches in the same row are from the same case and each row represents a different case.

Figure 6:
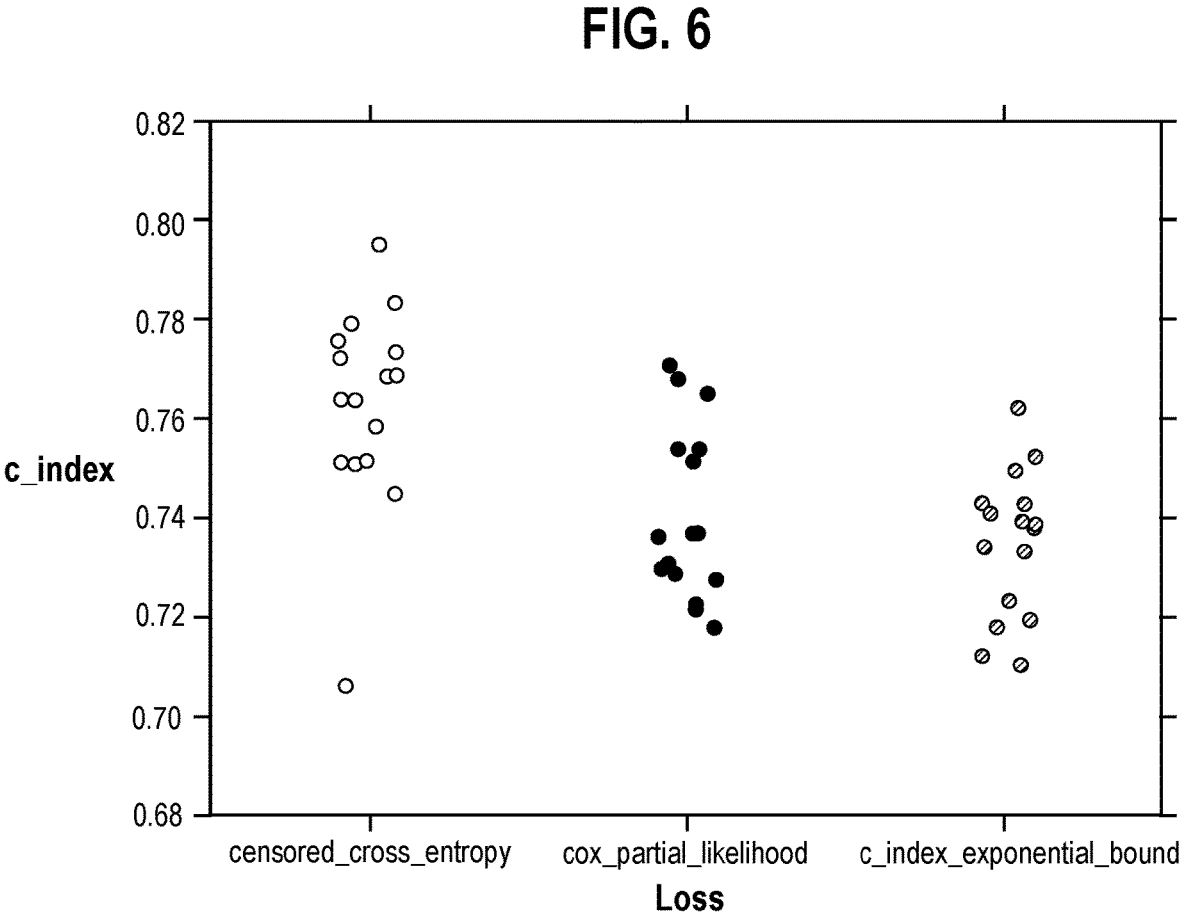
FIG. 6 is a plot showing a comparison of loss functions for DLS training.
Figure 7A:
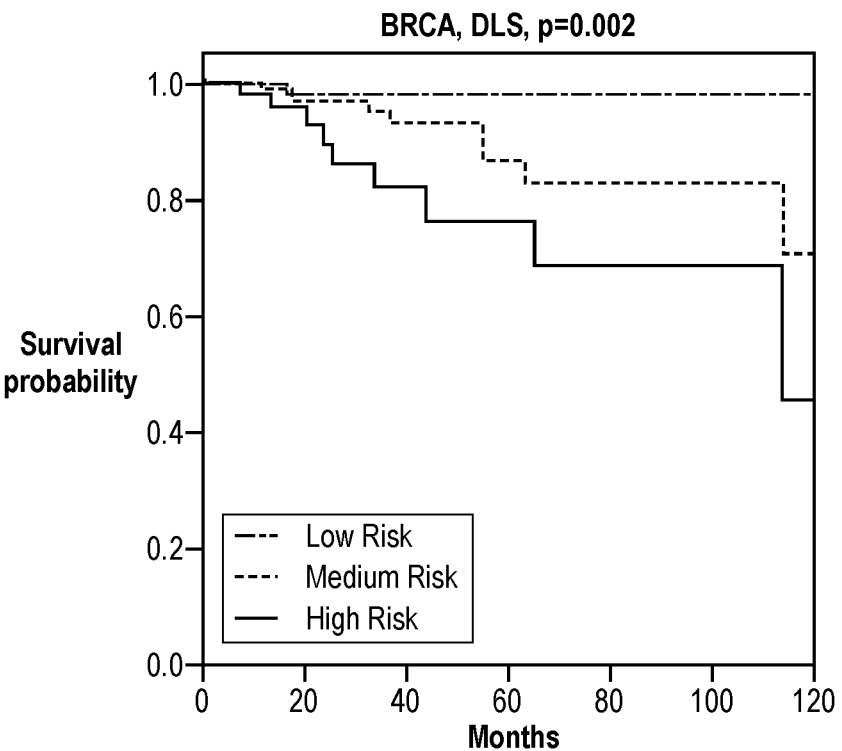
FIGS. 7A-7J are Kaplan Meier curves for DLS risk groups for each cancer type.
Figure 7B:
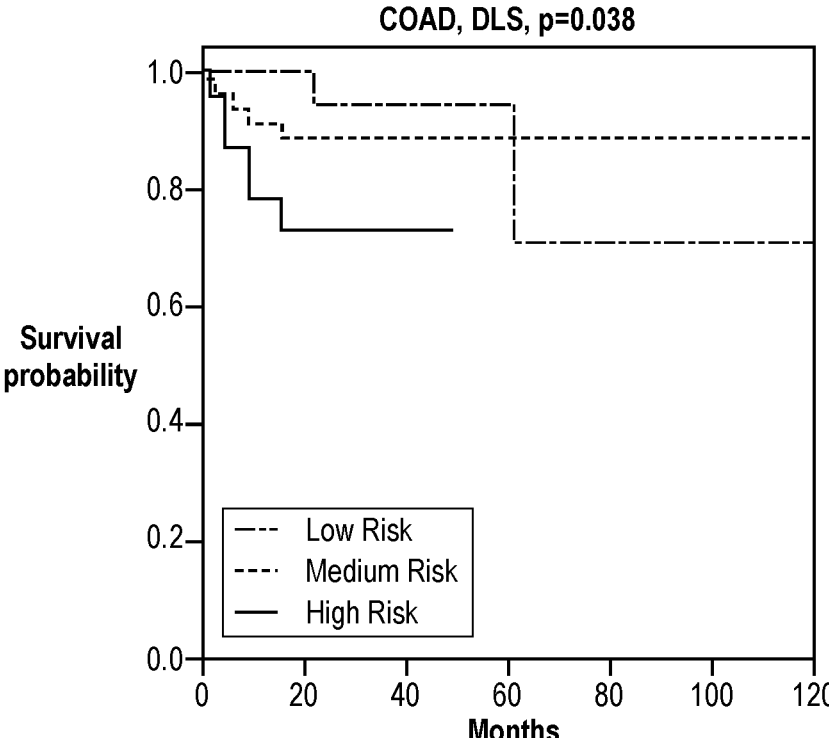
Figure 7C:
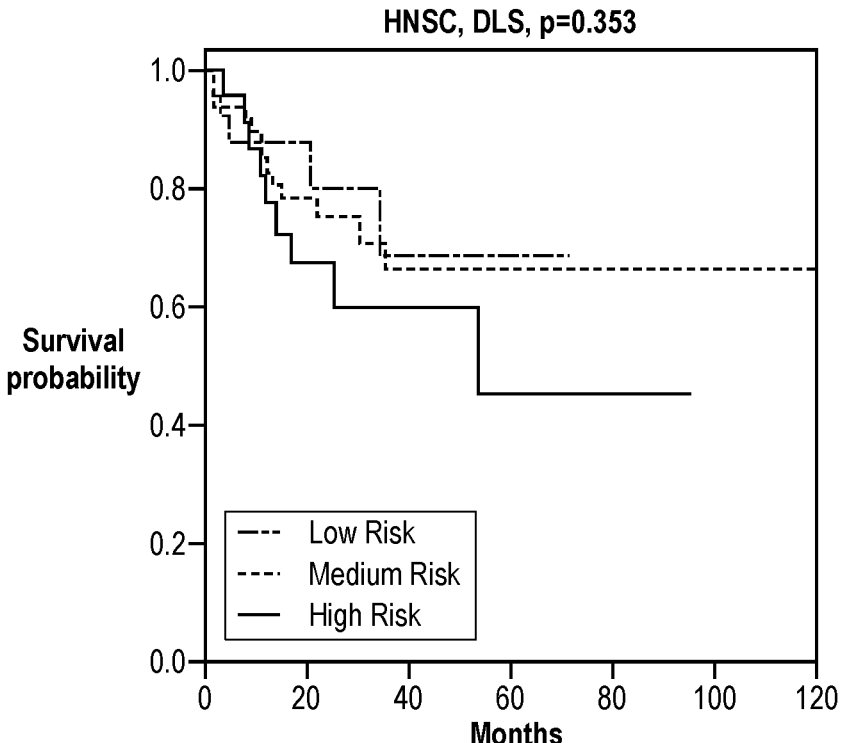
Figure 7D:
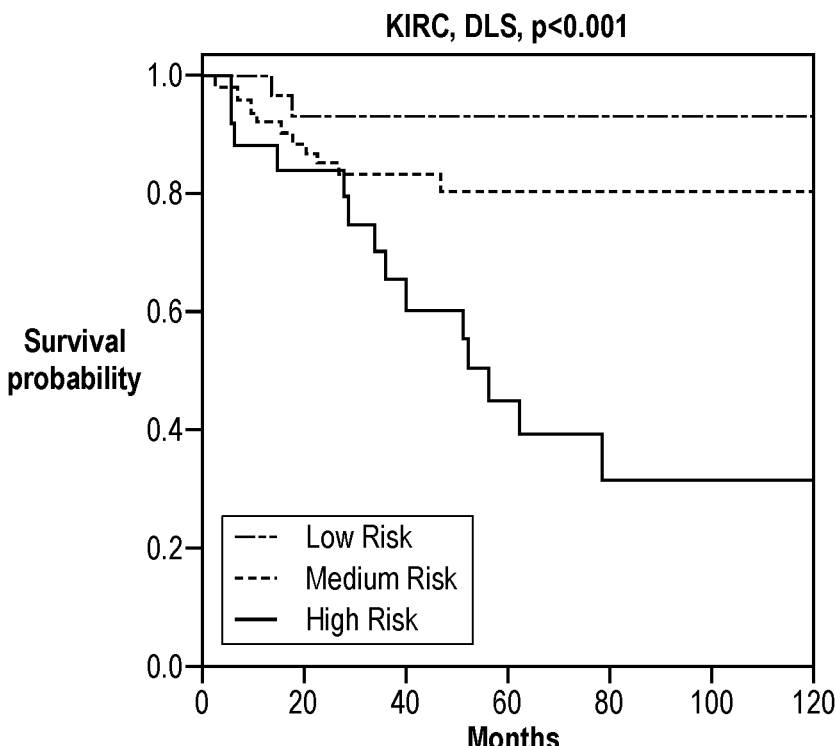
Figure 7E:
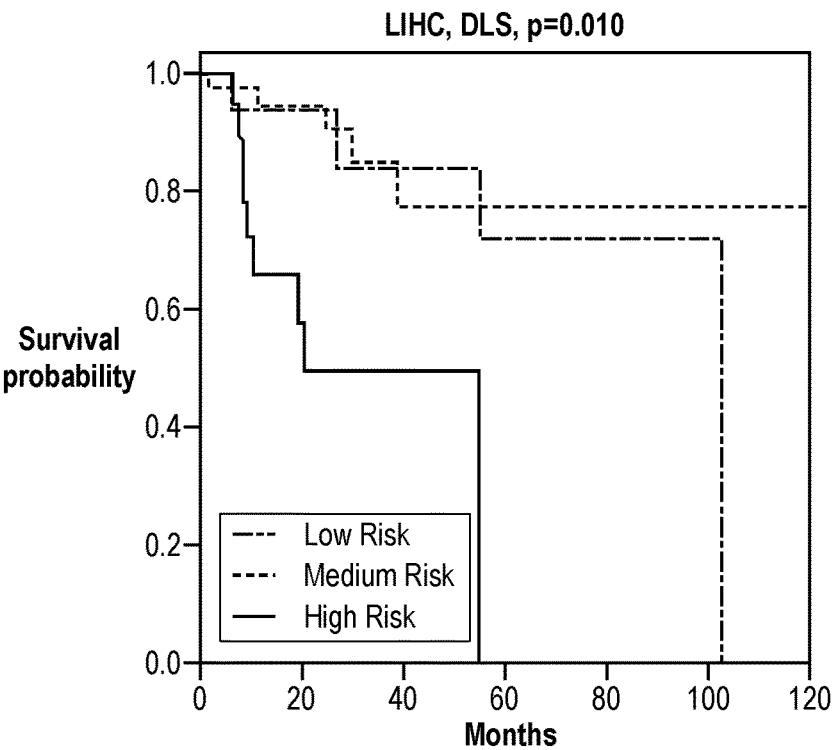
Figure 7F:
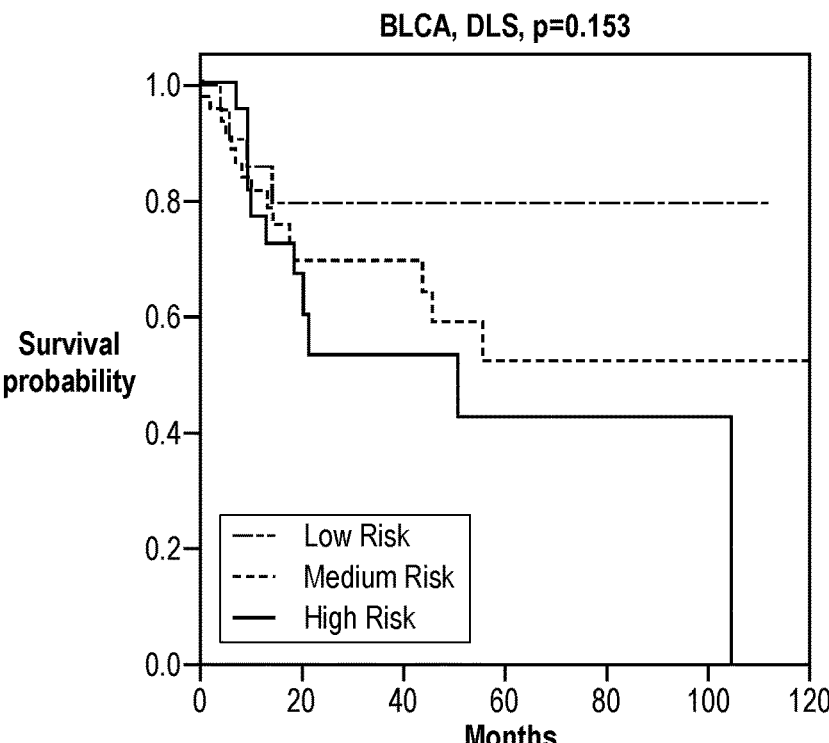
Figure 7G:
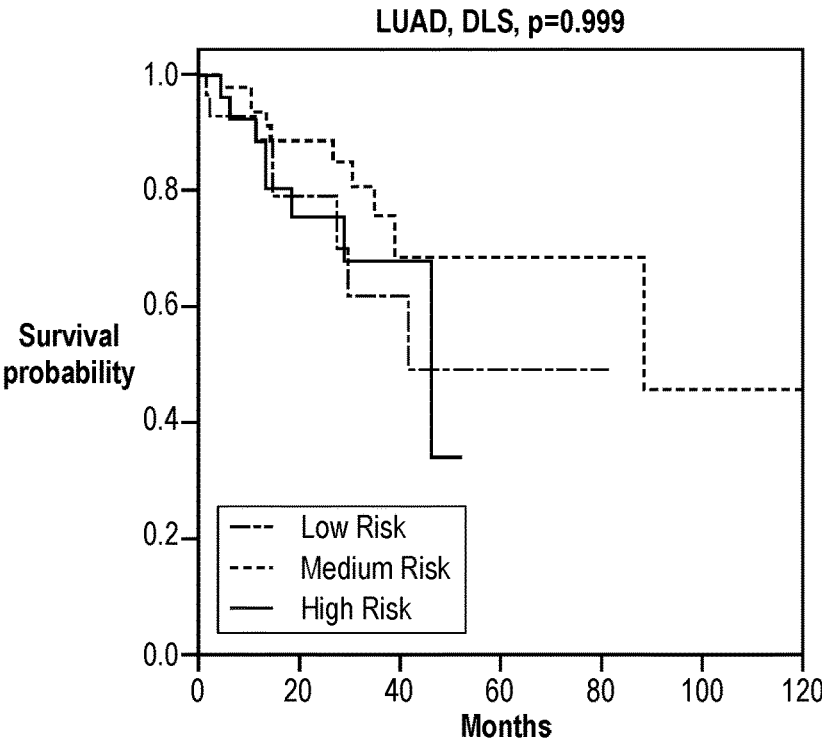
Figure 7H:
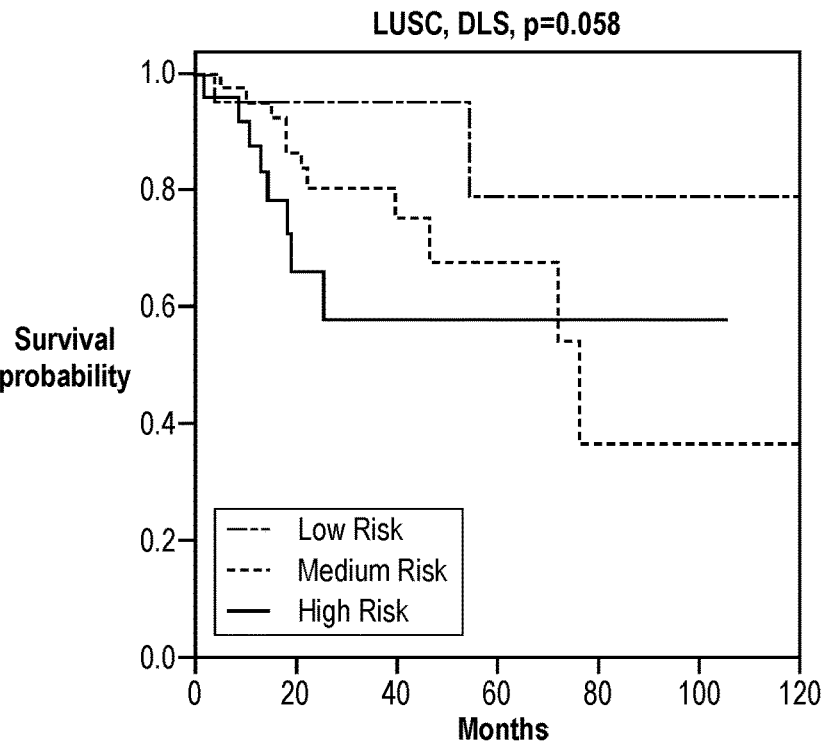
Figure 7I:
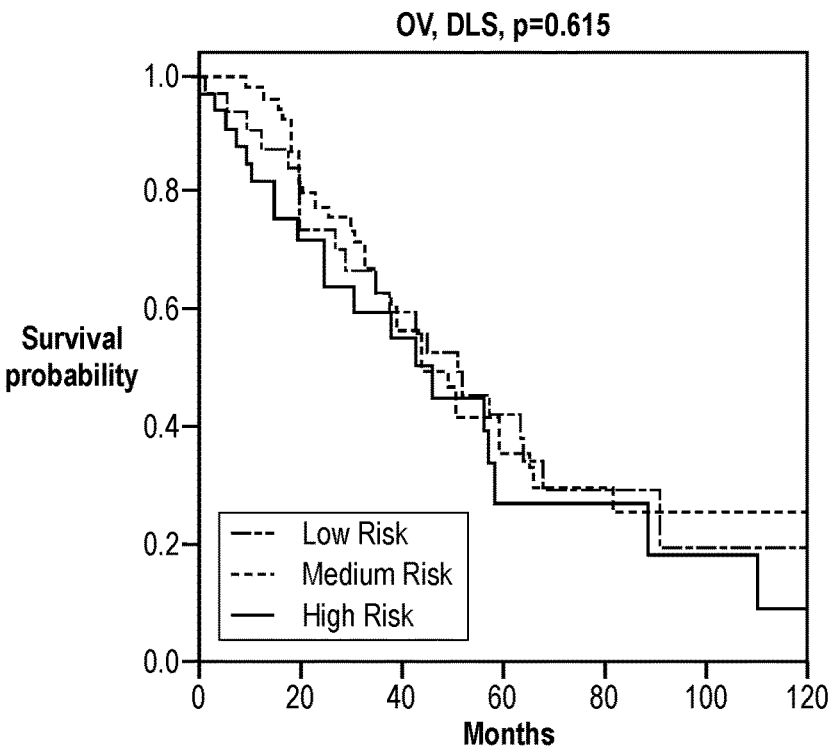
Figure 7J:
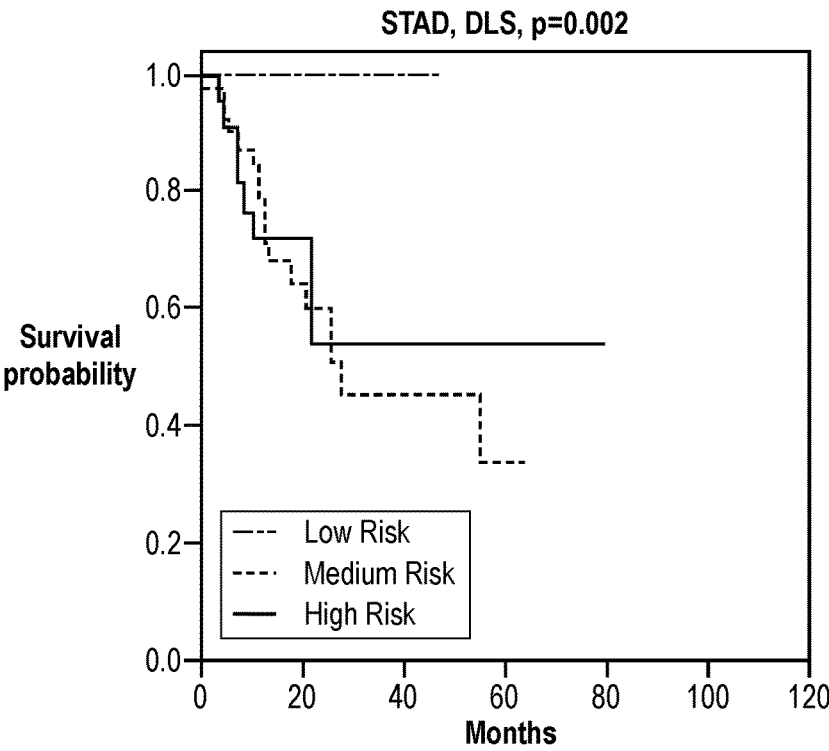

FIG. 6 is a plot showing a comparison of loss functions for DLS training. In this example, three loss functions for DLS training are compared: 1) censored cross-entropy, 2) Cox partial likelihood, 3) exponential lower bound on concordance index with the TCGA KIRC dataset. For each loss function 3 batch sizes (32, 64, 128) and 4 learning rates (10e-3, 5e-4, 10e-4, 5e-5, 10e-5) were tried. Models were evaluated on the tune split.

FIGS. 7A-7J are Kaplan Meier curves for DLS risk groups for each cancer type. FIGS. 7A-7E are plots for the five cancer types for which the DLS predictions was statistically significantly associated with disease specific survival in multivariable analysis.

Figure 8A:
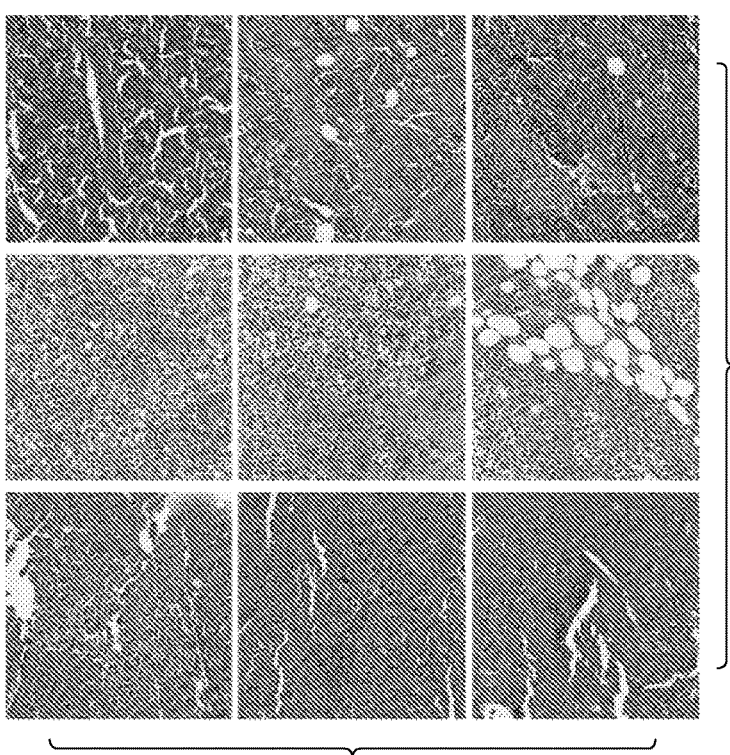
FIGS. 8A-8B illustrates visualization of image patches influencing survival prediction for breast invasive carcinoma (BRCA).
Figure 8B:
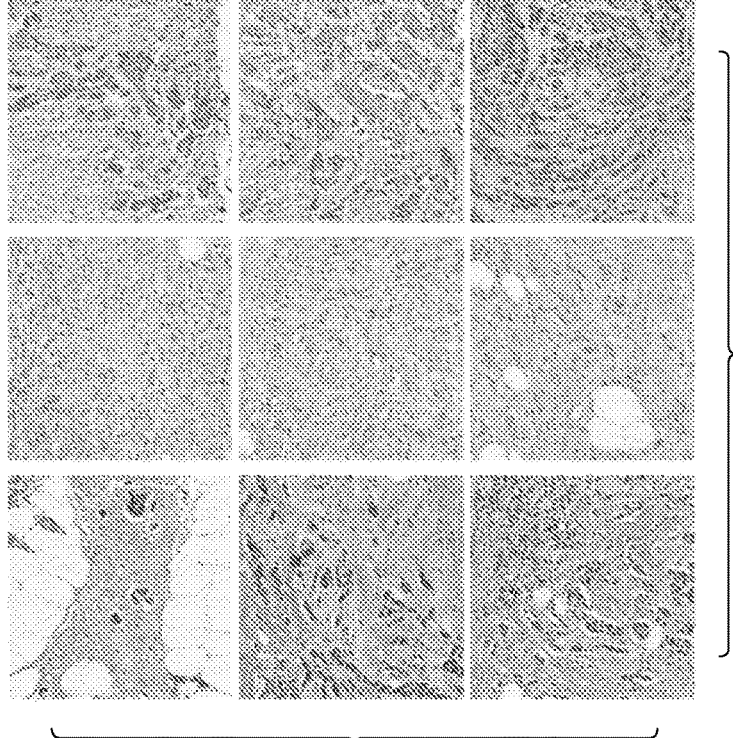

FIGS. 8A-8B illustrates visualization of image patches influencing survival prediction for breast invasive carcinoma (BRCA). High risk patches from highest risk cases (FIG. 8A) and low risk patches from lowest risk cases (FIG. 8B). Patches in the same row are from the same case and each row represents a different case.

Figure 9A:
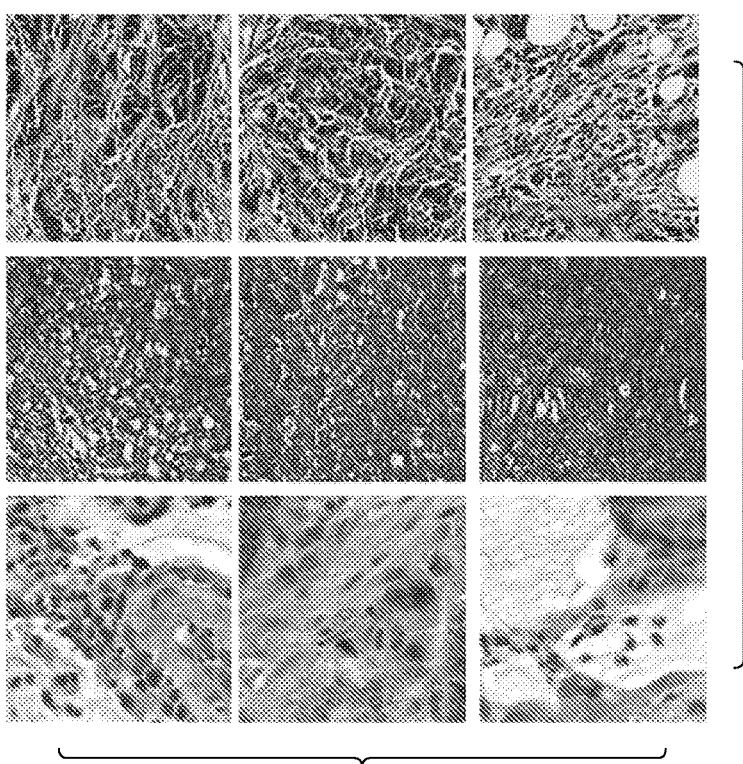
FIGS. 9A-9B illustrates visualization of image patches influencing survival prediction for colon adenocarcinoma (COAD).
Figure 9B:
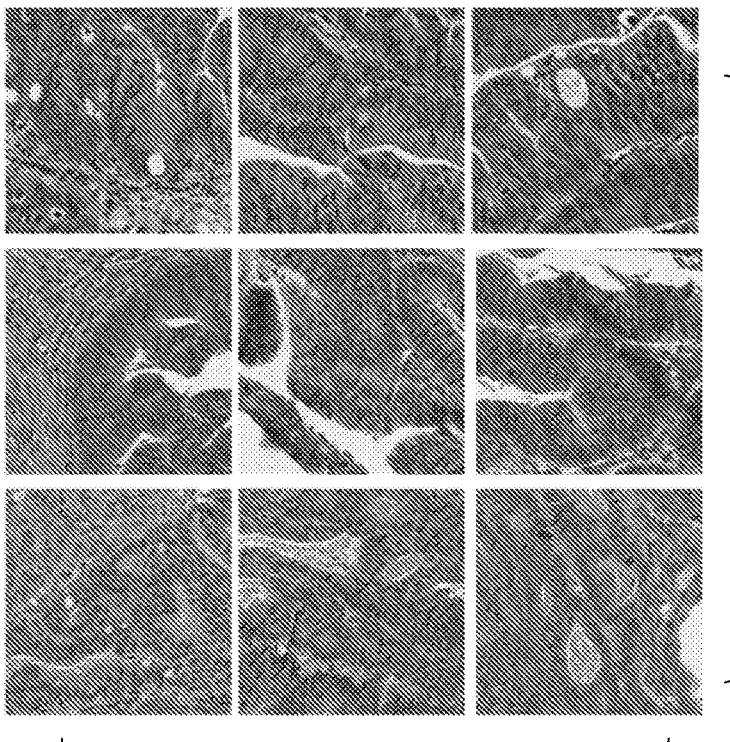

FIGS. 9A-9B illustrates visualization of image patches influencing survival prediction for colon adenocarcinoma (COAD). High risk patches from highest risk cases (FIG. 9A) and low risk patches from lowest risk cases (FIG. 9B). Patches in the same row are from the same case and each row represents a different case.

Figure 10A:
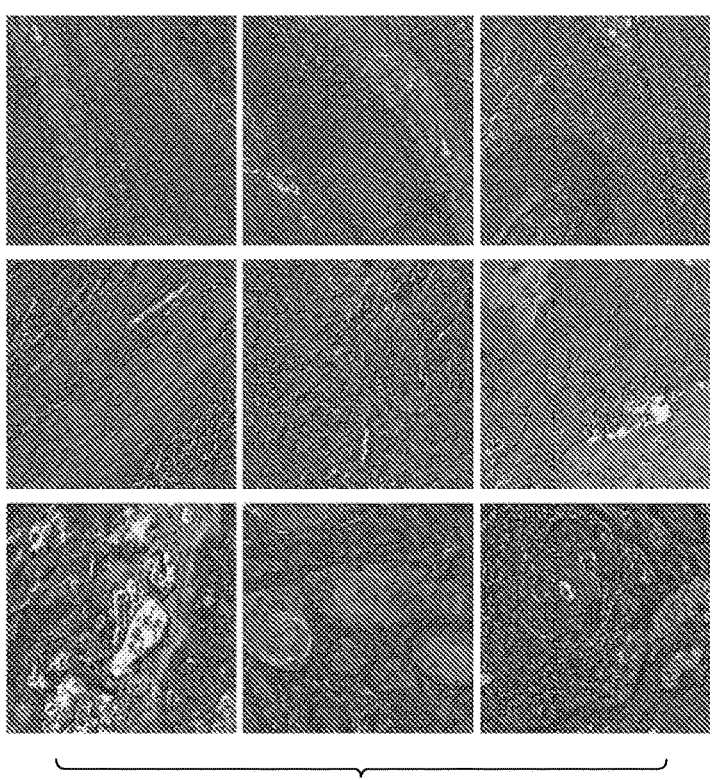
FIGS. 10A-10B illustrates visualization of image patches influencing survival prediction for head and neck squamous cell carcinoma (HNSC).
Figure 10B:
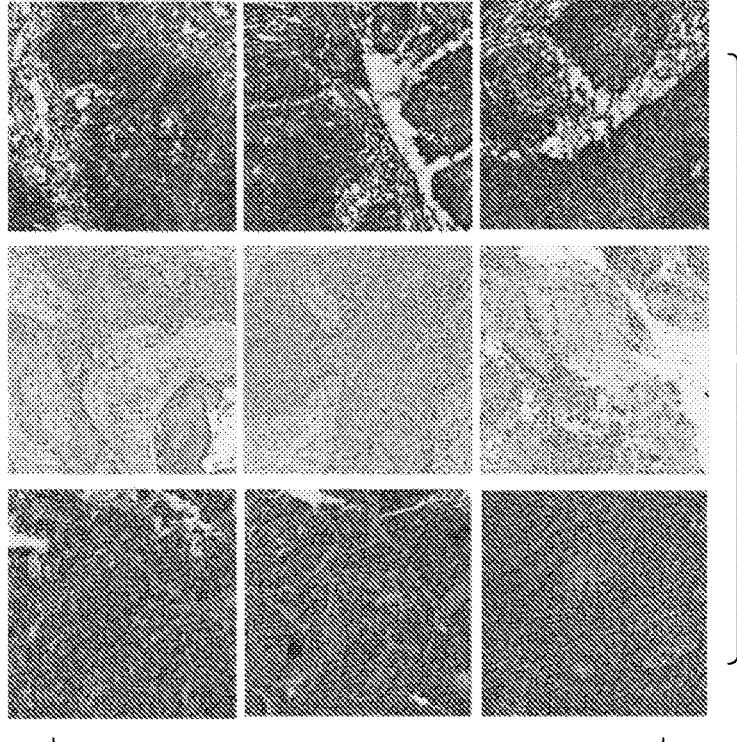

FIGS. 10A-10B illustrates visualization of image patches influencing survival prediction for head and neck squamous cell carcinoma (HNSC). High risk patches from highest risk cases (FIG. 10A) and low risk patches from lowest risk cases (FIG. 10B). Patches in the same row are from the same case and each row represents a different case.

Figure 11A:
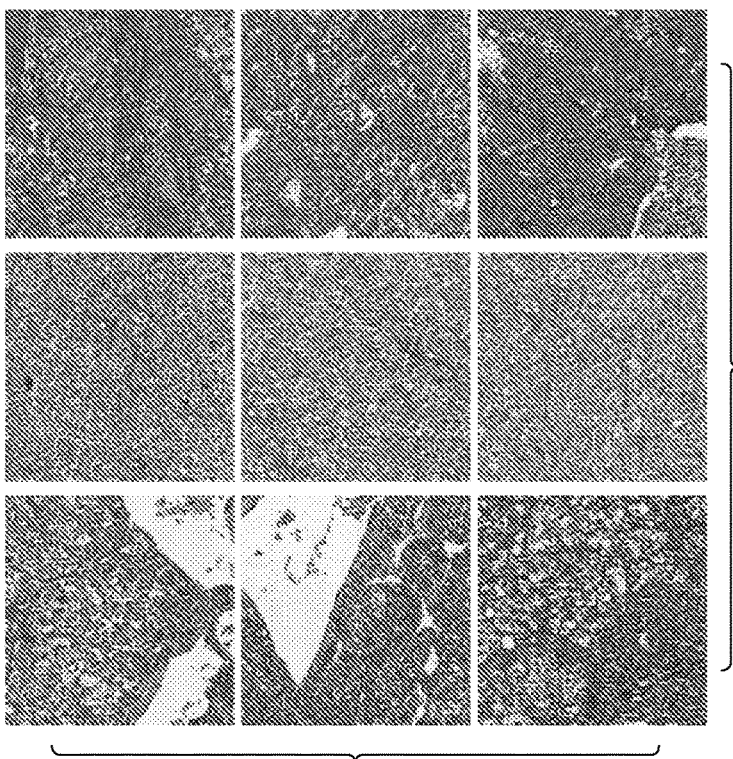
FIGS. 11A-11B illustrates visualization of image patches influencing survival prediction for liver hepatocellular carcinoma (LIHC).
Figure 11B:
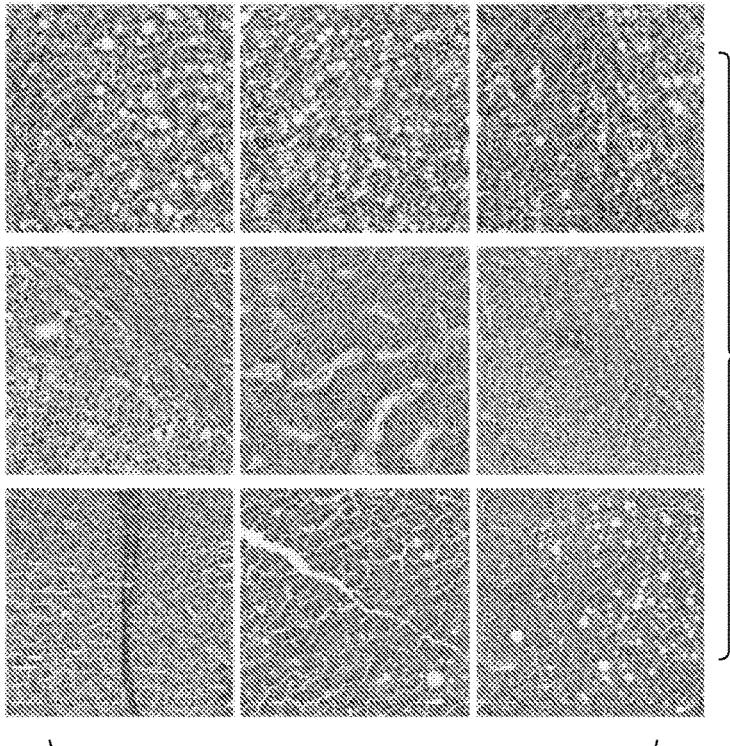

FIGS. 11A-11B illustrates visualization of image patches influencing survival prediction for liver hepatocellular carcinoma (LIHC). High risk patches from highest risk cases (FIG. 11A) and low risk patches from lowest risk cases (FIG. 11B). Patches in the same row are from the same case and each row represents a different case.

Figure 12:
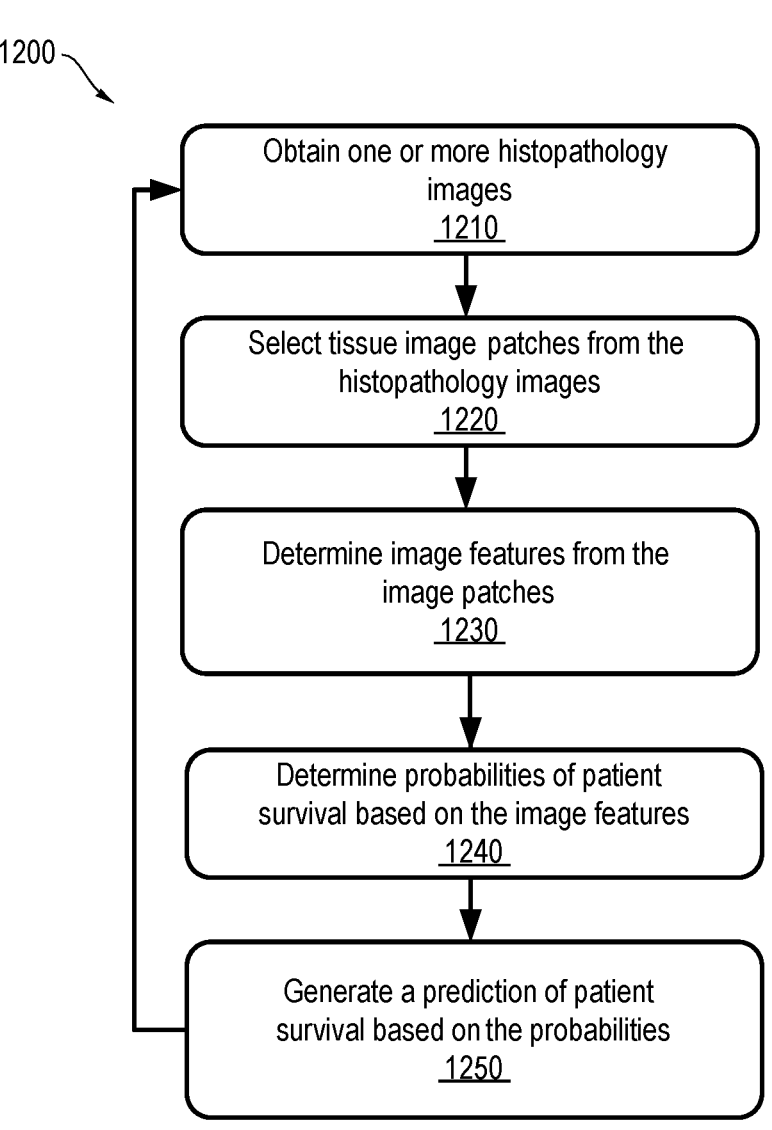
FIG. 12 shows an example method for directly predicting cancer patient survival based on histopathology images.

Referring now to FIG. 12, FIG. 12 shows an example method for directly predicting cancer patient survival based on histopathology images. The example will be discussed with respect to the system 200 shown in FIG. 2 and the DLS 100 shown in FIG. 1; however, any suitable system according to this disclosure may be employed.

At block, 1210, the computing device 210 obtains one or more histopathology images of a sample from a cancer patient. In this example, it obtains the images from its data store 212; however, in some examples, it may obtain the images from an imaging system or from a remote server 240 or data store 242.

At block 1220, the patch sampler 110 selects tissue image patches from the histopathology images. In this example, the patch sampler masks each image to remove any non-tissue portions of the image. Image patches are then extracted from each image corresponding to tissue portions of the image. In this example, the image patches are of uniform size; however, different examples may employ image patches of varying sizes. Further, in some examples, the image patches may be extracted randomly from the images, such as by randomly selecting portions of tissue to sample. However, in some examples, the random selection may relate to selecting which image patch to assign to which ML model 120a-n at block 1230.

At block 1230, the trained ML models 120a-n determine a plurality of image features for the plurality of tissue image patches. As discussed above, each image patch is supplied to one of the ML models 120a-n, which analyzes the image patch to identify feature values for the image patch.

At block 1240, the DLS 100 uses the averaging pool 140 and fully connected layer 140 to determine probabilities of patient survival based on the determined plurality of image features. As discussed above with respect to FIG. 1, the averaging pool 130 averages feature values for each feature channel and provides the averaged value to the fully connected layer 140. The fully connected layer 140 has been trained to determine probabilities of patient survival according to discrete bins, such as the four bins discussed above. Thus, the fully connected layer outputs the probability of patient survival for each bin.

At block 1250, the computing device 210 generates a prediction of patient survival based on the determined probabilities. In this example, the computing device 210 generates the prediction by outputting the probabilities received from the DLS 100 at block 1240. In some examples, however, the computing device 210 may output a single probability, such as the probability from the bin that has the highest probability value. Some examples, may determine if one bin has a probability that is much higher, e.g., based on a pre-defined threshold, than the other bins. If so, the prediction may be generated using that probability. Alternatively, if no probability is much higher than the others, the computing device 210 may output the top two probabilities determined at block 1240. Still other examples of generating a prediction of patient survival based on the determined probabilities may be employed.

In addition, the system may also generate a prediction of a molecular characteristic in the tissue sample. For example, as discussed above with respect to FIG. 1, the DLS 100 may be trained to recognize molecular characteristics, which may correspond with particular genetic mutations. Thus, in addition to generating the prediction of patient survival, the DLS 100 may also output whether a molecular characteristic is predicted and, in some examples, a potential corresponding genetic mutation.

Figure 13:
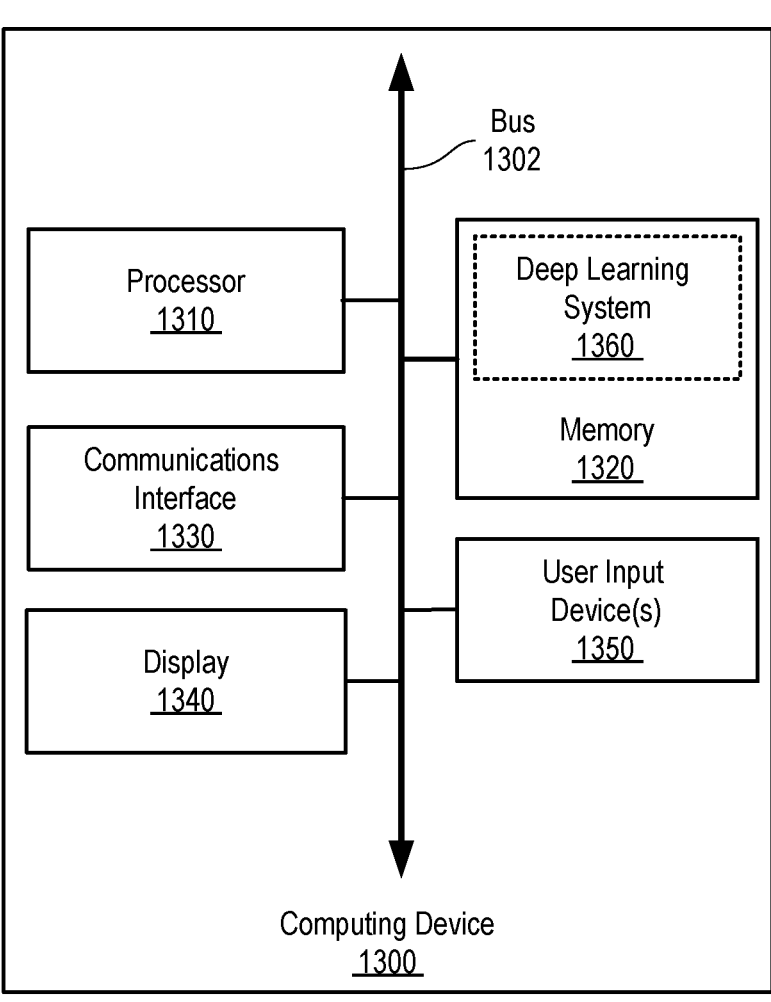
FIG. 13 shows an example computing device suitable for use with example systems and methods for directly predicting cancer patient survival based on histopathology images according to this disclosure.

Referring now to FIG. 13, FIG. 13 shows an example computing device 1300 suitable for use in example systems or methods for directly predicting cancer patient survival based on histopathology images according to this disclosure. The example computing device 1300 includes a processor 1310 which is in communication with the memory 1320 and other components of the computing device 1300 using one or more communications buses 1302. The processor 1310 is configured to execute processor-executable instructions stored in the memory 1320 to perform one or more methods for directly predicting cancer patient survival based on histopathology images according to different examples, such as part or all of the example method 1200 described above with respect to FIG. 12. In this example, the memory 1320 includes a deep learning system 1360, such as the example deep learning system 100 shown in FIG. 1. In addition, the computing device 1300 also includes one or more user input devices 1350, such as a keyboard, mouse, touchscreen, microphone, etc., to accept user input; however, in some examples, the computing device 1300 may lack such user input devices, such as remote servers or cloud servers. The computing device 1300 also includes a display 1340 to provide visual output to a user. However, it should be appreciated that user input devices or displays may be optional in some examples.

The computing device 1300 also includes a communications interface 1340. In some examples, the communications interface 1330 may enable communications using one or more networks, including a local area network ("LAN"); wide area network ("WAN"), such as the Internet; metropolitan area network ("MAN"); point-to-point or peer-to-peer connection; etc. Communication with other devices may be accomplished using any suitable networking protocol. For example, one suitable networking protocol may include the Internet Protocol ("IP"), Transmission Control Protocol ("TCP"), User Datagram Protocol ("UDP"), or combinations thereof, such as TCP/IP or UDP/IP.

While some examples of methods and systems herein are described in terms of software executing on various machines, the methods and systems may also be implemented as specifically-configured hardware, such as field-programmable gate array (FPGA) specifically to execute the various methods according to this disclosure. For example, examples can be implemented in digital electronic circuitry, or in computer hardware, firmware, software, or in a combination thereof. In one example, a device may include a processor or processors. The processor comprises a computer-readable medium, such as a random access memory (RAM) coupled to the processor. The processor executes computer-executable program instructions stored in memory, such as executing one or more computer programs. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example one or more non-transitory computer-readable media, that may store processor-executable instructions that, when executed by the processor, can cause the processor to perform methods according to this disclosure as carried out, or assisted, by a processor. Examples of non-transitory computer-readable medium may include, but are not limited to, an electronic, optical, magnetic, or other storage device capable of providing a processor, such as the processor in a web server, with processor-executable instructions. Other examples of non-transitory computer-readable media include, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may comprise code to carry out methods (or parts of methods) according to this disclosure.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

That which is claimed is:

1. A method comprising:
   obtaining one or more histopathology images of a sample from a cancer patient;
   selecting a plurality of tissue image patches from the one or more histopathology images;
   determining, by a deep learning system comprising a plurality of trained machine learning ("ML") models comprising a plurality of trained convolutional neural networks ("CNNs") having convolutional layers having shared weights and having outputs connected to an average pool, the average pool connected to a fully connected layer, a plurality of image features for the plurality of tissue image patches, wherein each tissue image patch is analyzed by one of the trained ML models;
   determining, by the deep learning system, probabilities of patient survival based on the determined plurality of image features; and
   generating, by the deep learning system, a prediction of patient survival based on the determined probabilities.

2. The method of claim 1, wherein the plurality of tissue image patches are randomly selected.

3. The method of claim 1, wherein the plurality of tissue image patches are uniformly sized.

4. The method of claim 1, wherein the trained CNNs were trained to predict prognosis from a set of training images in accordance with a survival loss function as a probability distribution over discretized survival times.

5. The method of claim 4, wherein the deep learning system is trained without requiring the leveraging of expert annotations or known features of interest in the training images.

6. The method of claim 4, wherein the survival loss function comprises censored cross-entropy function.

7. The method of claim 4, further comprising making a prediction of a molecular characteristic in a tissue sample.

8. The method of claim 7, wherein the molecular characteristic comprises a genetic mutation.

9. The method of claim 1, wherein the deep learning system is tuned with one or more hyperparameters comprising fixation types, patch size, patch set size, magnification, number of layers, base depth, L2 regularization weight, initial learning rate, thresholds, or training data sets.

10. A weakly supervised deep learning system for prediction of prognosis of a cancer patient, comprising:
   a non-transitory computer-readable medium; and
   a processor communicatively coupled to the non-transitory computer-readable medium, the processor configured to execute processor-executable instructions stored in the non-transitory computer-readable medium to:

21 obtain one or more histopathology images of a sample from a cancer patient;

randomly select a plurality of tissue image patches from the one or more histopathology images;

determine, by a deep learning system comprising a plurality of trained machine learning ("ML") models comprising a plurality of trained convolutional neural networks ("CNNs") having convolutional layers having shared weights and having outputs connected to an average pool, the average pool connected to a fully connected layer, a plurality of image features for the plurality of tissue image patches, wherein each tissue image patch is analyzed by one of the trained ML models;

determine, by the deep learning system, probabilities of patient survival based on the determined plurality of image features; and generate, by the deep learning system, a prediction of patient survival based on the determined probabilities.

11. The weakly supervised deep learning system of claim 10, wherein the plurality of tissue image patches are uniformly sized.

12. The weakly supervised deep learning system of claim 10, wherein the plurality of tissue image patches are randomly selected.

13. The weakly supervised deep learning system of claim 10, wherein the trained CNNs were trained to predict prognosis from a set of training images in accordance with a survival loss function as a probability distribution over discretized survival times.

14. The weakly supervised deep learning system of claim 13, wherein the deep learning system is trained without requiring the leveraging of expert annotations or known features of interest in the training images.

15. The weakly supervised deep learning system of claim 13, wherein the survival loss function comprises censored cross-entropy function.

16. The weakly supervised deep learning system of claim 13, wherein the system is further trained to make a prediction of a molecular characteristic in a tissue sample.

17. The weakly supervised deep learning system of claim 16, wherein the molecular characteristic comprises a genetic mutation.

18. The weakly supervised deep learning system of claim 10, wherein the deep learning architecture is tuned with one or more hyperparameters comprising fixation types, patch size, patch set size, magnification, number of layers, base depth, L2 regularization weight, initial learning rate, thresholds, or training data sets.

19. A weakly supervised deep learning system for prediction of prognosis of a cancer patient, comprising:

multiple convolutional neural networks modules having convolutional layers with shared weights, wherein each of the multiple convolutional neural networks accepts as input one cropped tissue image patch randomly selected from a histopathology image, an average pool receiving the output of each of the convolutional neural networks and a fully connected layer, wherein each of the multiple convolutional neural networks extracting features from each patch, the patch level features averaged on a per-channel basis in the average pool and fed to the fully connected layer, the multiple convolutional neural networks trained from training images comprising at least one histopathology image from each of a multitude of cancer patients to predict prognosis in accordance with a survival loss function as a probability distribution over discretized survival times, and wherein the deep learning system is trained without requiring the leveraging of expert annotations or known features of interest in the training images.

20. The weakly supervised deep learning system of claim 19, wherein the survival loss function comprises a censored cross-entropy function.

21. The weakly supervised deep learning system of claim 19, wherein the cancer patients have prostate cancer, breast cancer, colon cancer, head and neck squamous cell carcinoma, or liver hepatocellular carcinoma.

22. The weakly supervised deep learning system of claim 19, wherein the system is further trained to make a prediction of a molecular characteristic in a tissue sample.

23. The weakly supervised deep learning system of claim 22, wherein the molecular characteristic comprises a genetic mutation.

24. The weakly supervised deep learning system of claim 19, wherein the multiple convolutional neural networks are trained from at least one histopathology image from each of a multitude of cancer patients having a single type of cancer.

25. A system comprising a plurality of the weakly supervised deep learning system for prediction of prognosis of a cancer patient of claim 19, wherein each of the plurality of weakly supervised deep learning system is trained from the at least one histopathology image from each of a multitude of cancer patients having a single type of cancer, wherein the single type of cancer may be any of breast cancer, prostate cancer, colon cancer, head and neck squamous cell carcinoma, or liver hepatocellular carcinoma.

* * * * *